United States Patent
Yager et al.

(10) Patent No.: US 7,258,837 B2
(45) Date of Patent: Aug. 21, 2007

(54) MICROFLUIDIC DEVICE AND SURFACE DECORATION PROCESS FOR SOLID PHASE AFFINITY BINDING ASSAYS

(75) Inventors: Paul Yager, Seattle, WA (US); Elena Garcia, Seattle, WA (US)

(73) Assignee: University of Washington, Seattle, WA (US)

( * ) Notice: Subject to any disclaimer, the term of this patent is extended or adjusted under 35 U.S.C. 154(b) by 279 days.

(21) Appl. No.: 10/310,707

(22) Filed: Dec. 5, 2002

(65) Prior Publication Data

US 2003/0124623 A1 Jul. 3, 2003

Related U.S. Application Data

(60) Provisional application No. 60/337,606, filed on Dec. 5, 2001.

(51) Int. Cl.
| | |
|---|---|
| *G01N 21/00* | (2006.01) |
| *G01N 31/22* | (2006.01) |
| *G01N 33/00* | (2006.01) |
| *G01N 15/06* | (2006.01) |
| *G01N 33/53* | (2006.01) |
| *G01N 21/76* | (2006.01) |
| *G01N 1/18* | (2006.01) |
| *G01N 1/10* | (2006.01) |
| *B32B 5/02* | (2006.01) |
| *C12M 1/34* | (2006.01) |

(52) U.S. Cl. .................... 422/57; 422/58; 422/68.1; 422/81; 422/82.01; 435/7.9; 435/287.1; 435/287.2; 436/172; 436/177; 436/180

(58) Field of Classification Search ............... 422/57, 422/82.01, 81, 68.1; 436/180, 172, 177; 435/7.9, 287.2, 287.1
See application file for complete search history.

(56) References Cited

U.S. PATENT DOCUMENTS

| | | | |
|---|---|---|---|
| 5,716,852 A | 2/1998 | Yager et al. | 436/172 |
| 5,726,404 A | 3/1998 | Brody | 200/81 R |
| 5,726,751 A | 3/1998 | Altendorf et al. | 356/246 |

(Continued)

FOREIGN PATENT DOCUMENTS

GB    2341924    3/2000

(Continued)

OTHER PUBLICATIONS

Yager, P. et al., "Analytical devices based on transverse transport in microchannels," in Micro Total Analysis Systems 2000, Proceedings of μ TAS 2000 Symposium, held in Enschede, The Netherlands, May 14-18, 2000, pp. 15-18.

(Continued)

*Primary Examiner*—Long V. Le
*Assistant Examiner*—Jacqueline A. DiRamio
(74) *Attorney, Agent, or Firm*—Townsend and Townsend and Crew LLP

(57) ABSTRACT

This invention provides a microfluidic device for use in the detection of one or more analytes in a fluid using solid-phase affinity binding assays. The device offers a practical, easy-to-use, portable, inexpensive, robust analytical system for the parallel and quantitative detection of multiple analytes. In addition, this invention provides methods and devices for the formation of concentration gradients of capture molecules immobilized on a solid phase.

16 Claims, 12 Drawing Sheets

U.S. PATENT DOCUMENTS

| | | | |
|---|---|---|---|
| 5,747,349 A | 5/1998 | van den Engh et al. | 436/172 |
| 5,748,827 A | 5/1998 | Holl et al. | 385/134 |
| 5,815,278 A | 9/1998 | Johnston et al. | 356/445 |
| 5,822,073 A | 10/1998 | Yee et al. | 356/445 |
| 5,858,799 A | 1/1999 | Yee et al. | 436/164 |
| 5,922,210 A | 7/1999 | Brody et al. | 210/767 |
| 5,932,100 A | 8/1999 | Yager et al. | 210/634 |
| 5,948,684 A | 9/1999 | Weigl et al. | 436/52 |
| 5,971,158 A | 10/1999 | Yager et al. | 209/155 |
| 5,972,710 A | 10/1999 | Weigl et al. | 436/34 |
| 5,974,867 A | 11/1999 | Forster et al. | 73/61.41 |
| 5,991,048 A | 11/1999 | Karlson et al. | 356/445 |
| 6,007,775 A | 12/1999 | Yager | 422/57 |
| 6,039,897 A | 3/2000 | Lochhead et al. | |
| 6,067,157 A | 5/2000 | Altendorf et al. | 356/337 |
| 6,136,272 A | 10/2000 | Weigl et al. | 422/82.05 |
| 6,149,787 A | 11/2000 | Chow et al. | 204/451 |
| 6,159,739 A | 12/2000 | Weigl et al. | 436/52 |
| 6,221,677 B1 | 4/2001 | Wu et al. | 436/518 |
| 6,274,089 B1 | 8/2001 | Chow et al. | 411/101 |
| 6,408,884 B1 | 6/2002 | Kamholz et al. | 137/827 |
| 6,415,821 B2 | 7/2002 | Kamholz et al. | 137/827 |
| 6,480,282 B1 | 11/2002 | Chinowsky et al. | 356/445 |
| 6,482,306 B1 | 11/2002 | Yager et al. | 204/600 |
| 6,541,213 B1 | 4/2003 | Weigl et al. | 435/7.1 |
| 6,570,657 B1 | 5/2003 | Hoppe et al. | |
| 6,649,358 B1* | 11/2003 | Parce et al. | 435/7.2 |
| 6,875,619 B2* | 4/2005 | Blackburn | 436/514 |
| 6,900,021 B1* | 5/2005 | Harrison et al. | 435/7.21 |
| 2002/0041827 A1 | 4/2002 | Yager et al. | 422/57 |
| 2002/0076350 A1 | 6/2002 | Weigl et al. | 422/58 |
| 2002/0090644 A1 | 7/2002 | Weigl et al. | 435/7.1 |
| 2003/0124623 A1* | 7/2003 | Yager et al. | 435/7.5 |
| 2005/0238545 A1* | 10/2005 | Parce et al. | 422/100 |

FOREIGN PATENT DOCUMENTS

| | | |
|---|---|---|
| WO | WO 01/24933 | 4/2000 |
| WO | WO 0074850 | 12/2000 |

OTHER PUBLICATIONS

U.S. Appl. No. 60/421,917, filed Oct. 28, 2003, expired prov.
Anderson, J.R. et al., "Fabrication of topologically complex three-dimensional microfluidic systems in PDMS by rapid prototyping," (Jul. 2000) *Anal. Chem.* 72:3158-3164.
Becker, H. and L.E. Locascio, "Polymer microfluidic devices," (Feb. 2002) *Talanta* 56(2), 267-287.
Becker, H. and C. Gartner, "Polymer microfabrication methods for microfluidic analytical applications," (Jan. 2000) *Electrophoresis* 21(1):12-26.
Beebe, D.J. et al., "Physics and applications of microfuidics in biology," (Dec. 2002) *Annual Review of Biomedical Engineering* 4:261-286.
Berger, C.E.H., et al., "Resolution in surface plasmon microscopy," (1994) *Review of Scientific Instruments* 65: 2829-2837.
Brockman, J.M. et al., "Surface plasmon resonance imaging measurements of ultrathin organic films," (Oct. 2000) *Annual Reviews of Physical Chemistry* 51, 41-63.
Cabrera, C.R. (2002). "Microfluidic Electrochemical Flow Cells: Design, Fabrication, and Characterization", Thesis, Mar. 2002 Department of Bioengineering. Seattle, University of Washington.
Cabrera, C. R. et al., "Formation of natural pH gradients in a microfluidic device under flow conditions: model and experimental validation," (Feb. 2001) *Analytical Chemistry* 73(3):658-666.
Chabinyc, M.L. et al., "An integrated fluorescence detection system in poly(dimethylsiloxane) for microfluidic applications," (Sep. 2001) *Anal. Chem.* 73:4491-4498.
Chován, T. and A. Guttman, "Microfabricated devices in biotechnology and biochemical processing," (Mar. 2002) *Trends in Biotechnology* 20(3):116-122.

de Bruijn, H. E. et al., "Choice of metal and wavelength for surface-plasmon resonance sensors: some considerations," (1992) *Applied Optics* 31(4):440-442.
de Bruijn, H. E. et al. "Surface plasmon resonance microscopy: improvement of the resolution by rotation of the object," (1993) *Applied Optics* 32(13):2426-2430.
Dertinger, S.K.W. et al., "Generation of gradients having complex shapes using microfluidic networks," (Mar. 2001) *Anal. Chem.* 73(6):1240-1246.
Harrison, D.J. et al., "Towards miniaturized electrophoresis and chemical analysis systems on silicon: an alternative to chemical sensors," (1993) *Sensors and Actuators B: Chemical*, 10(2):107-116.
Hickel, W. and Knoll, W., "Surface plasmon microscopy of lipid layers," (1990) *Thin Solid Films* 187:349-356.
Hickel, W. and Knoll, W., "Time- and spatially resolved surface plasmon optical investigation of the photodesorption of Langmuir-Blodgett multilayer assemblies," (1991) *Thin Solid Films* 199:367-373.
Ismagilov, R.F. et al., "Microfluidic arrays of fluid—fluid diffusional contacts as detection elements and combinatorial tools," (Nov. 2001) *Anal. Chem.* 73:5207-5213.
Jandik, P. et al., "Initial study of using a laminar fluid diffusiin interface for sample preparation in high-performance liquid chromatography," (Apr. 2002) *Journal of Chromatography A*, 954:33-40.
Jeon, N.L. et al., "Generation of solution and surface gradients using microfluidic systems," (Oct. 2000) *Langmuir* 16:8311-8316.
Jung, L. S., et al., "Surface plasmon resonance measurement of binding and dissociation of wild-type and mutant streptavidin on mixed biotin-containing alkylthiolate monolayers," (1999) *Sensors and Actuators* 54:137-144.
Lichtenberg, J., et al., "Sample pretreatment on microfabricated devices," (Feb. 2002) *Talanta*, 2002. 56(2):233-266.
Love, J.C. et al., "Fabrication of three-dimensional microfluidic systems by soft lithography," (Jul. 2001) *MRS Bulletin* pp. 523-528.
Lyon, L. A. et al., "Surface plasmon resonance of colloidal Au-modified gold films," (1999) *Sensors and Actuators B* 54:118-124.
McDonald, J.C. and Whitesides, G.M., "Poly(dimethylsiloxane) as a material for fabricating microfluidic devices," (Jul. 2002) *Accounts of Chem. Res.* 35(7):491-499.
McDonald, J.C. et al., "Prototyping of microfluidic devices in poly(dimethylsiloxane) using solid-object printing," (Apr. 2002) *Anal. Chem.* 74(7):1537-1545.
McDonald, J.C. et al., "Fabrication of a configurable, single-use microfluidic device," (Dec. 2001) *Anal. Chem.* 73(23):5645-5650.
McDonald, J.C. et al., "Fabrication of microfulidic systems in poly(dimethylsiloxane)," (Jan. 2000) *Electrophoresis* 21(1):27-40.
Naimushin, A. N., et al., "Detection of *Staphylococcus aureus* enterotoxin B in femtomolar levels with a miniature integrated two-channel surface plasmon resonance (SPR) sensor," (2002) *Biosensors & Bioelectronics* 17:573-584.
Place, J. F. et al., "Opto-electronic immunosensors: a review of optical immunoassay at continuous surfaces," (1985) *Biosensors* 1:321-353.
Rothenhäusler, B. and Knoll, W., "Surface-plasmon microsopy," (1988) *Letters to Nature* 332: 615-617.
Shoji, S., "Fluids for sensor systems," (1998) *Topics in Current Chemistry* 194:163-188.
Verpoorte, E., Microfluidic chips for clinical and forensic analysis,: (Mar. 2002) *Electrophoresis*, 23(5), 677-712.
Wang, J., "On-chip enzymatic assays," (Mar. 2002) *Electrophoresis* 23(5):713-718.
Weigl, B.H. and P. Yager, "Microfluidic diffusion-based separation and detection," (1999) *Science*, 283:346-347.
Yager, P., et al., "Design of Microfluidic Sample Preconditioning Systems for Detection of Biological Agents in Environmental Samples", (1998) *SPIE* vol. 3515, Santa Clara, CA, pp. 252-259.
Löfås, S. et al., "Bioanalysis with surface plasmon resonance," *Sens. Actuators B Chem.*, 5:79-84 (1991).

* cited by examiner

MICROFLUIDIC DEVICE AND SURFACE DECORATION PROCESS FOR SOLID PHASE AFFINITY BINDING ASSAYS

CROSS REFERENCE TO RELATED APPLICATIONS

This application claims priority to U.S. provisional application Ser. No. 60/337,606 filed Dec. 5, 2001 which is hereby incorporated by reference in its entirety to the extent not inconsistent with the disclosure hereof.

SOURCES OF GOVERNMENT FUNDING

This work was funded, in part, by the U.S. Government. The U.S. Government may have some rights to certain aspects of the invention disclosed herein.

BACKGROUND

Solid phase affinity binding assays remain among the most versatile and rapid methods for detection of chemical and biological analytes from fluid samples. However, field deployment and point-of-care use of these diagnostic assays have historically been impractical because of the cost of instrumentation and test devices, complicated operation parameters and protocols, and lack of methods for robust storage of biological reagents, the degradation of which leads to poor assay performance.

Microfluidic systems offer solutions to many of these problems. Microfluidic systems and methods of use have been described in detail (Verpoorte, E., Electrophoresis, 2002 23(5), 677-712; Lichtenberg, J., et al., Talanta, 2002. 56(2),233-266; Beebe, D.J., et al., Annual Review of Biomedical Engineering, 2002,4, 261-286; Wang, J., Electrophoresis, 2002, 23(5), 713-718; Becker, H. and L.E. Locascio, Talanta, 2002, 56(2), 267-287; Chovan, T. and A. Guttman, Trends in Biotechnology, 2002. 20(3), 116-122; Becker, H. and C. Gartner, Electrophoresis, 2000, 21(1), 12-26; McDonald, J.C., et al., Electrophoresis, 2000, 21(1), 27-40; Weigl, B.H. and P. Yager, Science, 1999, 283, 346-347; and Shoji, S., Topics in Current Chemistry 1998, 194:163-188; U.S. Pat. Nos. 5,932,100; 5,922,210; 5,747,349; 5,972,710; 5,748,827; 5,726,751; 5,726,404; 5,716,852; 6,159,739; 5,971,158; 5,974,867; 6,007,775; 6,221,677; 5,948,684; 6,067,157; 6,482,306; 6,408,884; 6,415,821; and U.S. Patent Application Nos. 09/703,764 filed Nov. 11, 2000; 09/724,308, filed Nov. 28, 2000; 09/675,550, filed Sep. 27, 2000; 09/863,835, filed May 22, 2001; 09/428,839, filed Oct. 28, 1999; 09/723,823, filed Nov. 28, 2000; 09/503,563, filed Feb. 14, 2000; 09/574,797, filed May 19, 2000; 09/579,666, filed May 26, 2000; and 09/956,467, filed Sep. 18, 2001; all of which are incorporated herein in their entirety to the extent not inconsistent herewith).

Microfluidic systems for use in analyte detection in fluid streams have been studied extensively (e.g. U.S. Pat. Nos. 5,747,349; 5,716,852; 6,007,775; 5,984,684; and U.S. Patent Application No. 09/503,563 filed Feb. 14, 2000; Ser. No. 09/574,797, filed May 19, 2000; Ser. No. 09/863,835, filed May 22, 2000; and Ser. No. 09/724,308, filed Nov. 28, 2000). One fluid-phase analyte detection system utilizes methods for the solid-state storage and preservation of assay reagents in a microfluidic device, negating the need for multiple reagent sources external to the detection device (U.S. Pat. No. 6,007,775, incorporated herein in its entirety, to the extent not inconsistent herewith). Methods and devices for the electrokinetic control or transport of molecules in a microfluidic channel using electrophoresis, isoelectric focusing, and transverse electrophoresis have also been studied (e.g. Harrison, D. J., et al., Sensors and Actuators B: Chemical, 10(2), 107-116; and U.S. Patent Application No. 09/579,666 filed May 26, 2000).

Design of microfluidic systems using laminate technology allows multichannel analysis and the formation of 3-dimensional microfluidic systems of varying degrees of complexity (Jandik, P. et al. Journal of Chromatography A, 2002, 954: 33-40; Cabrera, C. (2002) "Microfluidic Electrochemical Flow Cells: Design, Fabrication, and Characterization", Thesis, 2002 Department of Bioengineering. Seattle, University of Washington; Cabrera, C. R., et al. Analytical Chemistry, 2001, 73(3), 658-666; Holl, M., et at., "Design of a Microfluidic Electrochemical Flow Cell", Electrophoresis, 2000 (submitted); Holl, M. R., et al., "Microfluidic device and methods for continuous-flow transverse electrokinetic separations", Electrophoresis (submitted); Yager, P., et al., "Design of Microfluidic Sample Preconditioning Systems for Detection of Biological Agents in Environmental Samples", SPIE, Santa Clara, CA; Yager, P., et al., "Analytical Devices Based on Transverse Transport in Microchannels"; Micro Total Analysis Systems 2000, University of Twente, the Netherlands, Kluwer Academic Publishers; Anderson; McDonald, J.C. and Whitesides, G.M., Accounts of Chemical Research, 35(7), 491-499; and McDonald, J.C., et at., Electrophoresis, 21, 27-40; all of which are incorporated herein in their entirety, to the extent not inconsistent herewith).

Solid phase microfluidic affinity binding assays have also been explored for their use with surface plasmon resonance (SPR) technologies to detect analyte binding within a microfluidic device (Jung, L. S., et al. Sensors and Actuators, 1999, 54,137-144; Lyon, L.A., et al. Sensors and Actuators B, 1999, 54, 118-124; Naimushin, A. N., et al., "Detection of Staphylococcus Aureus Enterotoxin B at Femtomolar Levels with a Miniature Integrated Two-channel Surface Plasmon Resonance (SPR) Sensor", Biosensors & Bioelectronics, 2002, 17:573-584; Place, J. F., et at., Biosensors, 1985, 1, 321-353, all of which are incorporated herein in their entirety to the extent not inconsistent herewith). Other SPR sensing devices have also been described for single or multiple analyte detection (U.S. Pat. Nos. 5,815,278; 5,822,073; 5,991,048; 5,858,799; and U.S. Patent Application Nos. 09/566,772 filed May 8, 2000; 60/1 32,893 filed May 6,1999; 60/1 32,895 filed May 6,1999; and 60/132,894 filed May 6,1999, all of which are incorporated herein in their entirety to the extent not inconsistent herewith).

It is often desirable to detect multiple analytes in parallel in a solid phase affinity binding assay. This parallel detection often involves complex protocols for the deposition and/or patterning of capture molecules on the binding surface. Such assays often require extensive development efforts for determining, for example, the optimum concentration of capture molecules bound to the solid phase.

There is a long felt need in the art of biological and chemical assays for a simple, easy-to-use, practical, inexpensive, compact, portable, versatile, and inexpensive device for performing quantitative bioassays in a variety of testing conditions, from controlled hospital and clinical environments to the often-extreme environments experienced by armed-forces personnel. Ideally, such devices perform parallel analysis of multiple analytes and require minimal development effort for determining optimal assay parameters.

SUMMARY OF THE INVENTION

This invention provides a microfluidic device for use in the detection of one or more analytes in a fluid using solid-phase affinity binding assays. The device offers a practical, easy-to-use, portable, inexpensive, robust analytical system for the parallel and quantitative detection of multiple analytes. In addition, this invention provides methods and devices for the formation of concentration gradients of capture molecules immobilized on a solid phase.

Specifically, this invention provides a microfluidic device for detecting the presence of an analyte in a fluid sample comprising:
   a) a microfluidic channel comprising a bottom wall, two side walls and a top wall and having an upstream end and a downstream end;
   b) a fluid inlet in fluidic connection with said microfluidic channel;
   c) a storage area on one of said walls of said microfluidic channel downstream of said fluid inlet;
   d) at least one solid reagent plug fixed in said storage area, said plug comprising a matrix and a reagent having an affinity for binding to said analyte; and
   e) a detection area within said microfluidic channel downstream of said fluid inlet and said storage area wherein said reagent binds to a binding wall of the microfluidic channel.

Numerous embodiments of the device of this invention exist, including those in which said storage area comprises a plurality solid reagent plugs immobilized in said storage area and wherein each reagent plug comprises one or a plurality of reagents. The storage areas can be arranged in parallel, series, or in a two-dimensional (2-D) array on one or more of the microfluidic channel walls. In addition, the microfluidic channel can comprise one or more additional inlets to the microfluidic channel from one or more tributary channels. The storage area can be any shape including but not limited to oval, round, triangular, square, star-shaped, trapezoidal or rectangular. The storage area can fill a portion of the wall, cross an entire wall perpendicular to the direction of fluid flow, or cross more than one wall.

The storage area can be a cavity within one or more walls positioned to allow the solid reagent plug to be dissolved by and diffuse into a carrier fluid flowing in the microfluidic channel, or the storage area can be a spot on the surface of one or more walls upon which the solid reagent plug is immobilized. Cavities can be any shape and, for example can be uniform, or can vary in width from top to bottom. The reagent can be surrounded by matrix and either dissolved by the flowing fluid, if it is soluble in the fluid, or suspended in the flowing carrier fluid if it is insoluble in the fluid.

In one embodiment of this invention, the binding wall of the microfluidic channel further comprises a coating that is adapted to bind specifically to one or more of the reagents. Alternatively, the coating can be one of the reagents. Alternatively, reagents bind 'passively' to an untreated binding wall through physisorption. In some embodiments of this invention, the reagent is a capture molecule having binding affinity for one or more analytes of interest. One or more of the reagents can also be a linking reagent, which can serve as a bridge between the binding wall and another reagent.

In other embodiments, at least a portion of one of the walls at the detection area is adapted for interrogation with detection systems selected from the group consisting of optical absorption, fluorescence intensity, fluorescence position, surface plasmon resonance (SPR), SPR microscopy, phosphorescence, chemiluminescence, electrochemiluminescence, attenuated total reflection, grating resonance, electrochemical detection, acoustic detection, and combinations thereof. Any of these detection schemes can utilize a single detector or an array of detectors. In particular, electrochemical detection and acoustic detection can utilize individual sensors (electrodes and acoustic detectors) or arrays of detectors integrated into or on one or more walls of the microfluidic channel.

For optical measurements, at least a portion of one of the walls in the detection area is transparent to light. For surface plasmon resonance techniques, at least a portion of the wall to which analyte binds is coated with a film of metal capable of supporting surface plasmons. Such metal films, and their deposition/coating on solid supports is well known in the art.

In other embodiments, at least a portion of two opposite walls of the microfluidic channel comprises electrodes. These electrodes can be formed in the walls of the microfluidic channel by any method known in the art, including evaporative deposition, electroplating, electroless deposition, or by placement of pre-cut metal parts. In one embodiment, the electrodes are positioned downstream of the storage area and upstream of the detection area, preferably with one of the electrodes on the same wall as the binding wall. Alternatively, the metal-coated binding wall adapted for surface plasmon resonance detection serves as one of the two electrodes. In other embodiments, more than two electrodes are used in an array for electrochemical detection. Each wall having an electrode on it can have one, two, three, or more electrodes separated from each other, wherein all of the electrodes on a given wall are electrically connected to each other to form an electrode group. This electrode group can also be electrically connected to a single electrode or electrode group on the opposite wall.

This invention further provides a method for storing a reagent in a microfluidic device comprising the steps of:
   a) providing a microfluidic device comprising:
      i) a microfluidic channel comprising a bottom wall, two side walls and a top wall and having an upstream end and a downstream end; and
      ii) a storage area on one of said walls of said microfluidic channel downstream of said fluid inlet;
   b) forming a first reagent solution comprising the reagent and a matrix material;
   c) depositing the reagent solution in the storage area; and
   d) converting the reagent solution in the storage area from a fluid to a solid to form a solid reagent plug and to form a microfluidic device of this invention.

Steps b-d can be repeated at least once to form two or more solid reagent plugs in the storage area. The solid reagent plugs can be deposited on the same spot or within the same cavity to form a layered plug, or they can be deposited in different spots or in different cavities.

The step of converting the reagent solution to a solid plug comprises dehydration of the reagent solution (which comprises reagent(s) and matrix component(s)). Dehydration can be effected by any method that removes some or all of the water from the reagent solution in a controlled manner. Methods include simple storage in low-humidity air, or in a vacuum, an oven, a hood, or any combination thereof. Upon dehydration, one or more matrix-forming compounds in the reagent solution replace the waters of hydration that are removed from around the reagent. Other matrix components can be used to form a glass-like solid upon dehydration that encases the dehydrated reagent. Alternatively, hydrogel-forming compositions can be used as the matrix component and the step of converting the reagent solution to a solid reagent plug comprises gelation wherein the solid reagent plug is a hydrogel. Suitable hydrogel compositions include alginate or other hydrogels subject to dissolution when exposed to a buffer not containing an ingredient necessary for gelation.

The reagent solution can be deposited on the storage area of the microfluidic channel using any method known in the art, including but not limited to the use of a pin tool, a capillary tube, or ink jet printing techniques.

In one embodiment of this invention, the reagent solution further comprises a monitoring agent such as Prodan (6-propionyl-2-dimethylaminonaphthalene), or another indicator known to the art, the optical properties of which change in response to the degree of hydration of their environment, thus allowing the conversion of the reagent solution from fluid to solid to be monitored.

In yet another embodiment, an already dehydrated solid reagent plug can be introduced and immobilized to a storage area on the microfluidic device.

This invention also provides a method for immobilizing a reagent in a microfluidic channel, comprising the steps of:
 a) providing a microfluidic device of this invention comprising a solid reagent plug;
 b) flowing a fluid into said microfluidic channel through an inlet; and
 c) allowing the matrix surrounding the reagent in the solid reagent plug to dissolve in the flowing solution.
 whereby the dissolved or suspended reagent forms a plume in the flowing fluid and is carried to the detection area and immobilized on the binding wall.

In some embodiments of this immobilization method, a concentration gradient of immobilized reagent is formed at the binding wall.

When this method is practiced with a microfluidic device having more than one storage area, the storage areas can be positioned such that the plumes formed by the dissolution of the solid reagent plugs are isolated from each other and the immobilized reagents do not overlap on said binding wall. Alternatively, the storage areas can be positioned such that some portion of the plumes overlap along some or all of the length of the microchannel and the immobilized reagents also overlap along at least a portion of the binding wall.

This invention also provides a method for detecting an analyte in a fluid sample using any of the microfluidic devices of this invention comprising the steps of:
 a) providing a microfluidic device of this invention comprising a solid reagent plug comprising a matrix and a reagent that is a capture molecule having affinity for said analyte;
 b) flowing a first fluid into the microfluidic device;
 c) dissolving the solid reagent plug with said flowing fluid, whereby the solid reagent plug is dissolved in the first fluid and the dissolved or suspended reagent is carried to the detection area and immobilized to the binding wall;
 d) flowing a sample fluid into said microfluidic device, said sample fluid comprising the analyte to be detected, whereby said analyte is bound to said capture reagent;
 e) detecting said bound analyte.

When this method is practiced with a microfluidic device having more than one storage area, the storage areas can each comprise different capture reagents having affinity for different analytes, thereby allowing simultaneous detection of multiple analytes. The method can further comprise the step of determining the concentration of the analyte in the sample fluid.

Additional reagents can also be used that comprise secondary binding reagents. The dissolution of plugs containing these reagents can be delayed until after analyte binding has occurred, or in the case of a microfluidic device having a tributary channel connected to the microfluidic channel via a second inlet, the solid reagent plug containing the secondary binding reagent can be located in the tributary channel, and will not dissolve until fluid is flowed through the tributary channel through a second inlet and into the microfluidic channel. Alternatively, a secondary reagent can be stored on the same storage area as a capture reagent, e.g. as a solid reagent plug forming the bottom layer in a cavity, wherein the top layer comprises a solid reagent plug having capture molecules.

Further, the method of detecting uses a method selected from the group consisting of: optical absorption measurement, fluorescence intensity measurement; fluorescence intensity measurement as a function of position along the binding wall, surface plasmon resonance, surface plasmon resonance microscopy, phosphorescence, chemiluminescence, electrochemiluminescence, attenuated total reflection, grating resonance, electrochemical detection, acoustic detection and combinations thereof. Other detection methods known in the art can also be adapted for use with the microfluidic device of this invention.

This invention further provides an analyte detection system comprising:
 a) any of the embodiments of the microfluidic device of this invention;
 c) a fluid handling system in fluidic connection with a sample source and an inlet of a microfluidic channel of this invention; and
 d) a detection system in optical connection with the detection area.

The analyte detection system further optionally comprises a computer coupled to a light source and a detector and optionally coupled to said fluid handling system.

The fluid handling system can be any fluid handling system known in the art capable of delivering fluid to an inlet of a microfluidic channel and effecting its flow through the channel. In one embodiment of this method, the fluid handling system is a positive displacement pump. Other fluid handling systems include hydrostatic pressure heads, electrokinetic pumping means, or any of a wide range of mechanical pumps internal or external to the microfluidic device itself.

The analyte detection system can further comprise a device holder to secure the microfluidic device in optical connection with the detection system and/or the fluid handling system and optionally translate the detection area relative to the detection system.

In one embodiment of the analyte detection system, at least a portion of the binding wall is coated with a metal to form a metallic interior surface and the optical detection system comprises:
 a) a light source coupled to said binding wall through a prism whereby surface plasmon waves are excited at the metallic interior surface of said binding wall; and
 b) a detector positioned to detect light reflected from the metallic surface of said binding wall through said prism.

Alternatively, at least one wall of the detection area is transparent to light and the optical detection system comprises:
 a) a light source optically coupled to said detection area; and
 b) a detector optically coupled to said detection area.

Also provided is a method of making the microfluidic device of this invention, comprising the steps of:

a) providing a first substrate layer;
c) providing a second layer in contact with said first substrate layer wherein said second layer comprises a microfluidic channel having an inlet, a bottom wall and two side walls;
d) providing a third layer in contact with said second layer such that said third layer forms a top wall; and
e) immobilizing a solid reagent plug to one of said walls downstream of said fluid inlet to form a storage area.

This method can further comprise the step of providing a further layer disposed between the substrate layer and the second layer, said further layer comprising a substrate with a cavity disposed thereon wherein the second layer further comprises a hole in alignment with the further layer.

DETAILED DESCRIPTION OF THE INVENTION

Figure 1A:
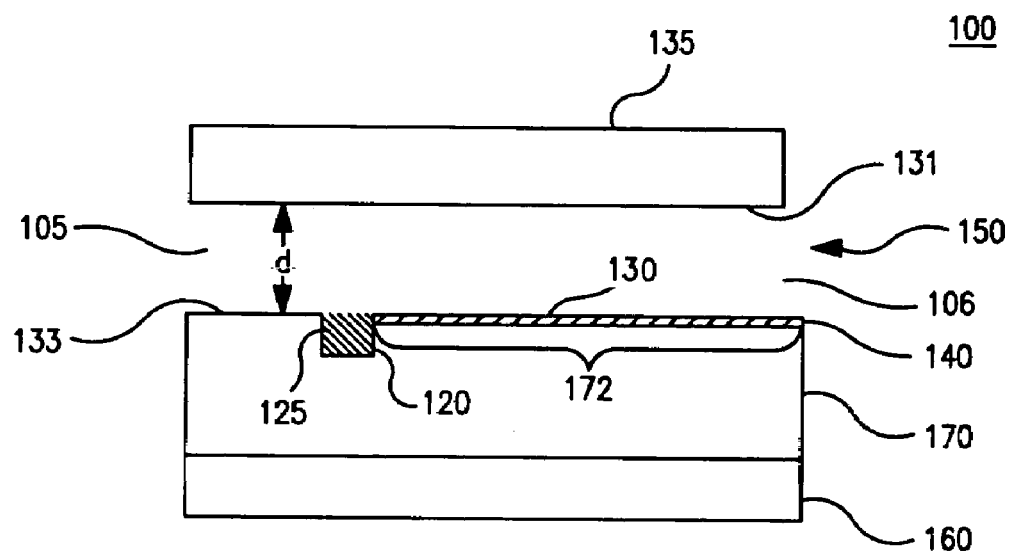
FIGS. 1A-1D are side views of the microfluidic device of this invention and illustrate the use of this device in a solid phase affinity binding assay.

The term "microfluidic" as used herein refers to a flow channel, or a device containing a flow channel, in which at least one of the channel dimensions is less than 1 mm. Flow is "laminar" in microfluidic devices comprising microfluidic channels of a size such that the Reynolds number for flow within the channel is below about 1, preferably below about 0.1. Reynolds number is the ratio of inertia to viscosity. Low Reynolds number means that inertia and turbulence are essentially negligible. Flow can be laminar with Reynolds number greater than 1. However, such systems are prone to developing turbulence when the flow pattern is disturbed, e.g., when the flow speed of a stream is changed, or when the viscosity of a stream is changed. Microfluidic channels used in the device of this invention can be straight or convoluted.

The term "solid phase affinity binding assay" is used herein to refer to any affinity assay in which the analyte of interest is bound to a solid substrate. Typical solid phase affinity binding assays include, but are not limited to immunoassays (analyte capture, sandwich, competitive, and others) and nucleic acid binding assays. Other assays include functional protein complex assays using protein arrays in which a series of proteins thought to be targets for binding by other, unknown proteins are arrayed as spots across a surface. The unknown proteins are introduced to the arrayed target proteins and binding (the formation of a protein complex) is detected. Solid phase assays are also used to determine which proteins bind to promoter sequences in genes, by arraying specific DNA sequences on the solid phase, introducing proteins, and detecting which proteins bind to which DNA sequences. Numerous other solid phase assays are known in the art, and may be practiced with the device and methods of this invention.

"Inlets" comprise openings into a microfluidic channel. Inlets can fluidically connect a microfluidic channel to tributary microchannels, which are branching channels off of a main microfluidic channel, and may also be connected to tubes, syringes, pumps, and the like which provide means for injecting or otherwise introducing fluid into the microfluidic device. Outlets comprise openings out of a microfluidic channel and can also be connected to collection ports, absorbent material and/or means for removing fluid from the outlet, including receptacles for the fluid, means for inducing flow, such as by capillary action, pressure, gravity, and other means known to the art.

The term "plurality" as used herein refers to a number greater than one.

The term "fluid" refers to any substance that will readily assume the shape of the container in which it is held. Fluids include gases and liquids.

The terms "in fluid connection with" or "in fluid communication with" mean that fluid is capable of flowing between the two or more elements which are in fluid connection with each other.

A "reagent" comprises any chemical compound, biological molecule, or combinations thereof. Reagents include species that are utilized in an affinity binding assay or utilized to monitor the operation of the microfluidic device of this invention. Reagents include, but are not limited to, capture molecules, linking molecules, secondary binding molecules, and reporter molecules. "Capture molecules" or "capture reagents" are any molecules, including biomolecules and biopolymers, that have binding affinity for an analyte molecule of interest, including but not limited to, drugs, enzymatic inhibitors, hormones, antibodies and other proteins, and nucleic acid probes. "Secondary binding molecules" also have binding affinity for an analyte molecule, and are often used in sandwich-type affinity binding assays. "Reporter molecules" are any molecules that are used to enhance the detection of analyte in a solid phase affinity binding assay, and can include optically absorbing, fluorescent, phosphorescent, chemiluminescent, and electroluminescent materials, and chromophores. Reagents also include calibration chemicals (e.g. internal standards of an analyte of interest), chemicals to monitor the flow rate in the microfluidic device and dissolution rate of the solid reagent plug, pH indicators, and other reagents typically used in microfluidic devices or affinity binding assays. Reagents can also include particulate materials such as polymeric, metallic, or other microspheres or nanoparticles used to monitor flow or solid reagent plug dissolution. Particulate reagents can also have chemically reactive, or other binding groups immobilized on the particle surface, or buried within the particle.

Such particulate reagents dissolve in a fluid flowing over the solid reagent plug, or are suspended in the fluid as the matrix materials dissolve.

The term "solid" refers to a material that will not flow, or is not fluid. Solid also refers to a material from which enough liquid has been removed to prevent its flow. A material does not have to undergo complete dehydration (removal of all water) to be considered a solid.

The term "matrix" or "matrix-forming" refers to all of the non-reagent chemicals or materials that comprise the reagent solution, or in its solid form, the reagent plug. The matrix comprises the chemicals that surround the reagent upon dehydration, either on a molecular scale by replacing the waters of hydration around the reagent, or on a bulk scale by forming a glass-like solid that encases the dehydrated reagent. The matrix includes preservatives such as trehalose, glass-forming carbohydrates such as dextran, and hydrogel-forming compositions among others. Matrix materials are preferably inert, i.e. they do not react with the reagents that they surround.

The term "preservative" as used herein is any chemical compound or mixtures of chemical compounds that can replace the waters of hydration surrounding a reagent or regents upon removal of water from a solution of the reagent or reagents or otherwise preserve the function and/or viability of the reagent during storage.

The term "dissolution" when used in reference to the dissolution of the solid reagent plug, means that the solid reagent plug is re-hydrated, the matrix material dissolves, and the reagent is either dissolved (if soluble in the re-hydrating fluid) or is suspended in the re-hydrating fluid.

The term "analyte" as used herein refers to chemical compounds, small molecules, particles, ions, cells, viruses, fungi, bacteria, and biomolecules and biopolymers (e.g. nucleic acids, antibodies, and proteins), and other materials whose presence or quantity it is desirable to detect. The term "biomolecule" as used herein is meant to include the term "biopolymer".

The term "storage area" refers to an area on one or more walls of a microfluidic channel in which a reagent is stored. The storage area can be a spot formed on one or more walls, or a cavity within one or more walls, and can be any shape.

A "binding wall" is one or more walls on a microfluidic channel on which the solid phase affinity binding assay is performed.

A "detection area" is a portion of the microfluidic channel, downstream of the storage area, that comprises the binding wall. It is the area in which analytical detection methods are used to detect analyte binding to the binding wall, or to detect a control signal from an area of no analyte binding.

The term "parallel" when used to refer to the relative arrangement of structures in a microfluidic channel means that the structures are arranged across one or more microchannel walls in the direction perpendicular to the flow direction.

The term "series" when used to refer to the relative arrangement of structures in a microfluidic channel means that the structures are arranged on a microchannel wall in the same direction as fluid flow.

The terms "array" or "two-dimensional array" are used herein to indicate that multiple elements (e.g capture molecules, solid reagent plugs, electrodes, detectors and the like) are placed within or on a microfluidic channel at defined locations.

The term "detection system" encompasses the elements necessary for the detection of analyte bound at the binding wall in the detection area. Optical detection systems, for example, include at least one light source, at least one detector, and all filters, lenses, prisms and other optical components. The detection system can optionally include a computer for optics control, data collection from the detector, and/or data analysis. Electrical detection systems include electrodes for transfer of charge to or from chemicals in solution, and circuitry for measuring either potential or current or both that flow through each of the electrodes in the array. In addition, electrical detection systems include some form of electronic system that converts the current or voltage into a digitized signal for subsequent display and analysis.

This invention provides devices and methods for the rapid, qualitative and/or quantitative parallel detection of single or multiple analytes utilizing the principles of microfluidics and solid phase affinity binding assays.

Method for Storing Labile Biomolecular Reagents on a Microfluidic Device

It is possible to store chemical reagents in solid form (dried, or partially dried) in a cavities or on spots on a solid substrate, to be allowed to enter a flowing stream in a controlled manner by controlled dissolution of the matrix surrounding the reagents. This method can be employed for storage of complex biomolecules, including antibodies, avidin, nucleic acid probes, or any reagent used in solid phase affinity binding assays, including reporter molecules, small molecule substrates or enzyme inhibitors, among others. Other reagents that can be stored include positive controls for calibration of the microfluidic device, pH indicators useful in detecting reactions in the microfluidic channel, and labels such as fluorescent markers that are used to monitor flow rate within the microfluidic device, or dissolution rate of a solid reagent plug.

This invention provides methods for the storage and preservation of affinity binding assay reagents, as well as their distribution to and immobilization on a solid phase. In many embodiments, the reagent is a capture molecule that has specific affinity for binding to an analyte of interest. The stored reagent can also be a linking molecule that has an affinity for one or more capture molecules. Such capture and linking molecules are well known in the art of affinity binding assays. Capture molecules include, but are not limited to antibodies, cell surface receptors, other proteins, tethered small molecules, and nucleic acid probes. Linking molecules include, but are not limited to avidin, nucleic acid probes, and a variety of chemical linking groups. As used herein, the term "avidin" includes all known forms of avidin, including native avidin, streptavidin, and any other modified or engineered form of avidin.

The microfluidic device of an embodiment of this invention comprises one or more microfluidic channels having one or more storage areas positioned along the "entrance" edge of the device between the inlet and a detection area. In each storage area is positioned a dry solid reagent plug or plugs comprising reagent dispersed in a matrix of a dry but soluble preservative such as a carbohydrate, e.g. a sugar such as trehalose. Trehalose and related sugars substitute for waters of hydration of biomolecules and other reagents in solution and allow the dehydration (removal of the waters of hydration) of biomolecules and other reagents and their long-term storage under any environmental condition without loss of function. Trehalose, as a non-reducing sugar, is preferred to reducing sugars that can modify proteins through chemical reactions with protein lysine residues. Any ratio of reagent to the components in the matrix can be used that allows the long-term storage of the reagent without loss of its function. Any compound capable of substituting the waters of hydration around a reagent can be used as the preservative component of the matrix.

In addition to sugars such as trehalose, the matrix may also comprise dextran. In addition to being a bulking agent, dextran can improve storage stability because its glass transition temperature is higher than that of trehalose (Allison, S. D., et al., *J. Pharm. Sci.*, 2000, 89(2), 199-214) and allows a more controllable dissolution of solid reagent plugs. In preferred embodiments of this invention, the matrix comprises both trehalose and dextran.

Solid reagent is immobilized in or on the storage area by: delivery to the storage area (e.g. to the bottom of storage cavity(ies)) of a concentrated reagent solution (a concentrated solution of the reagent and any matrix-forming components), followed by conversion of the liquid solution to a solid by dehydration, gelation of a solution containing a suitable gelation composition, or a combination of the two methods. Methods of dehydration are well known in the art, and include, but are not limited to simple evaporation (or evaporation in a laminar flow hood), heating, application of a vacuum, or any combination thereof. This immobilizes the capture molecule on the storage spot(s), or in the storage cavity(ies) as a glass-like solid plug.

The conversion of the reagent solution to a solid reagent plug can optionally be monitored by the addition of a suitable environmentally-sensitive probe to the solution. For example, Prodan (6-propionyl-2-dimethylaminonaphthalene) can be added to the solution, with or without a hydrophobic solvent, to quantify the water content present in the solution by monitoring the peak shift of the fluorescence as a function of water removal. As water is removed from a solution containing Prodan, the fluorescence peak due to the Prodan shifts to shorter wavelengths. Other probes can also be used, as long as a detectable property of the probe changes with the degree of hydration.

Control of the drying conditions (e.g. rate of dehydration) can allow the creation of different topologies (cracked, smooth, bumpy, and the like) of the exposed surface of the solid reagent plug, which can affect the flow of fluid across the solid reagent plug, and thus the distribution of reagent across the microfluidic device. It is also possible to achieve similar effects on fluid flow across the plug by using different shaped cavities (e.g. cylindrical, square, pyramidal, hemispherical, and the like).

Once the reagent solutions are rendered solid by any acceptable method, the reagents are very robust with respect to storage. Note that it is possible to layer two or more plugs on top of each other in a single cavity to allow sequential release of different reagent molecules from a single cavity. Multiple reagent plugs can also be positioned on one or more walls of the microfluidic channel, in parallel, series, or in a two-dimensional array.

The composition of the matrix can also be varied to affect the dissolution rate of a solid reagent plug when a fluid flows over it. For example, addition of increasing amounts of dextran to the reagent solution increases the time necessary for dissolution. This is particularly useful if, for example, one of the reagents is a secondary binding molecule, and it is desirable to delay the dissolution of the secondary binding reagent plug until after a capture reagent (present in another storage area, or layered in a cavity on top of the secondary reagent plug) is immobilized on the binding wall and analyte has bound to the capture reagent.

To use the reagent molecules for their intended purpose the microfluidic channel is placed in contact with a flowing, preferably aqueous, carrier fluid that will fill space (if any) above the solid reagent plug in the cavity, resulting in the dissolution of the matrix. Upon dissolution of the matrix, reagent is either also dissolved by the carrier fluid, or if it is insoluble, suspended in the carrier fluid.

Microfluidic Method for Immobilizing Capture Molecules in a Pattern on a Solid Phase An important aim of many sensor systems is detection of multiple analytes in parallel. One option is to decorate different detection zones on a surface with different capture molecules. This is often called an array-based approach. The detection surface may have multiple discrete zones that display different chemistries. Array-forming methods include spotting, ink-jet printing, and lithographic printing. We provide a novel method of producing multiple zones of capture molecules that also includes an extremely simple method of producing gradients of the surface concentration of those capture molecules.

In low Reynolds number conditions (laminar flow), the flow of fluid across the opening of each storage cavity (or spot) produces a smooth flow of fluid through each cavity that dissolves the matrix of the solid reagent plug embedded therein from the top of the cavity down. The fluid flow carries a plume of capture molecules, for example, downstream where they become available by diffusion to a binding wall surface for binding to the binding wall. In some embodiments, the binding surface is activated prior to exposure to the reagent molecules to increase the binding efficiency and viability of the reagent molecules. The efficiency of binding depends in part on the occupancy of surface sites. For example, a clean gold surface captures proteins by their natural or intentionally-introduced surface thiol groups. An alternative is to pre-coat the binding wall with an avidin monolayer, which can then capture biotinylated reagent molecules with high efficiency. Other such linking strategies are well known in the art, and include methods to prevent the crowding of capture molecules on a surface which can decrease the viability of the capture molecules, and ultimately their capacity for binding analyte.

The flow pattern and velocity immediately over a solid reagent plug will vary as the solid reagent plug shrinks. The dissolution rate of the solid reagent plug (and, therefore, the plume characteristics of the reagent it contains) can be varied by modification of the shape of the cavity or by layering different matrix/reagent mixtures. The fraction of the reagent molecules from the cavity that are bound by the surface depends on the flow rate and diffusivity of those molecules, as well as the capacity of the surface to bind them. The use of a plurality of storage areas allows the decoration of a binding wall with a selected large number of capture molecules.

FIGS. 1A-1D are side views of the microfluidic device of this invention and illustrate the use of this device in a solid phase affinity binding assay. These drawings are not to scale. FIG. 1A illustrates microfluidic channel 150 having top wall 131 formed by coverplate 135 and bottom wall 133 formed by substrate 170. The distance 'd' is defined as the channel thickness in the direction perpendicular to the flow direction. Substrate 170 may be formed from a single layer or may be a laminate structure formed from two or more layers of the same or differing materials. Substrate 170 may be adhered to base 160 to add support to the laminate structure. The walls of microfluidic channel 150 can be formed from materials such as glass, silicon, poly(dimethylsiloxane) (PDMS), Mylar, and any other materials that can adhere to each other using some form of bonding (including the use of adhesives). When desirable, or necessary for certain optical detection methods, the walls are made from materials transparent to the light source used in the detection system.

Flow in microfluidic channel 150 is from left to right, from inlet 105 to outlet 106. Storage area 120 is pictured as a cavity on bottom wall 133, but the storage area could also be a spot on bottom wall 133. As pictured, storage area 120 contains solid reagent plug 125. At least a portion of bottom wall 133 downstream of storage area 120 forms detection area 172 within which area is binding wall 130. Binding wall 130 is optionally formed by coating bottom wall 133 with a thin layer of metal (preferably gold) 140. This metal layer is any thickness suitable for use with surface plasmon resonance detection. Preferably the layer is made of gold and is about 40 nm to about 60 nm thick. (Note that these drawings are not to scale. In practice, the layer of metal does not form a noticeable 'lip' at the edge of storage area 120)

Figure 1B:
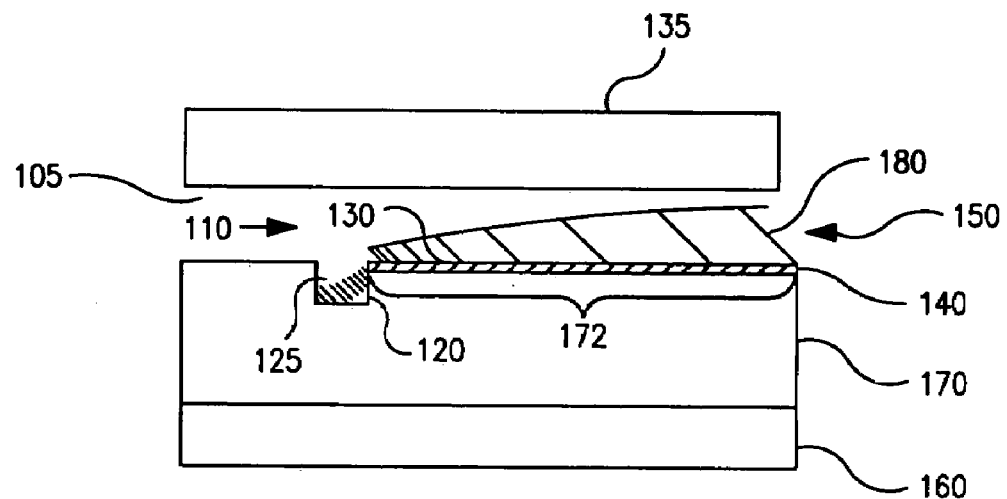
Figure 1C:
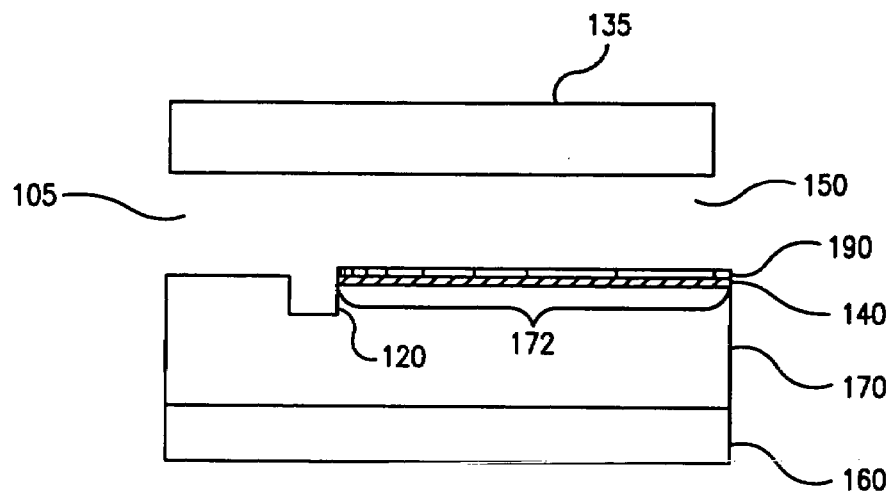

FIG. 1B illustrates the wetting of microfluidic channel 150 with a first carrier fluid 110 through inlet 105. Carrier fluid 110 flows over storage area 120 causing the matrix component of reagent plug 125 to dissolve within carrier fluid 110. As the carrier fluid travels downstream of storage area 120, the dissolved or suspended reagent diffuses within the carrier fluid, creating reagent plume 180. Reagent molecules from reagent plume 180 bind to binding wall 130 to form a concentration gradient of bound reagent 190 (FIG. 1C).

Figure 1D:
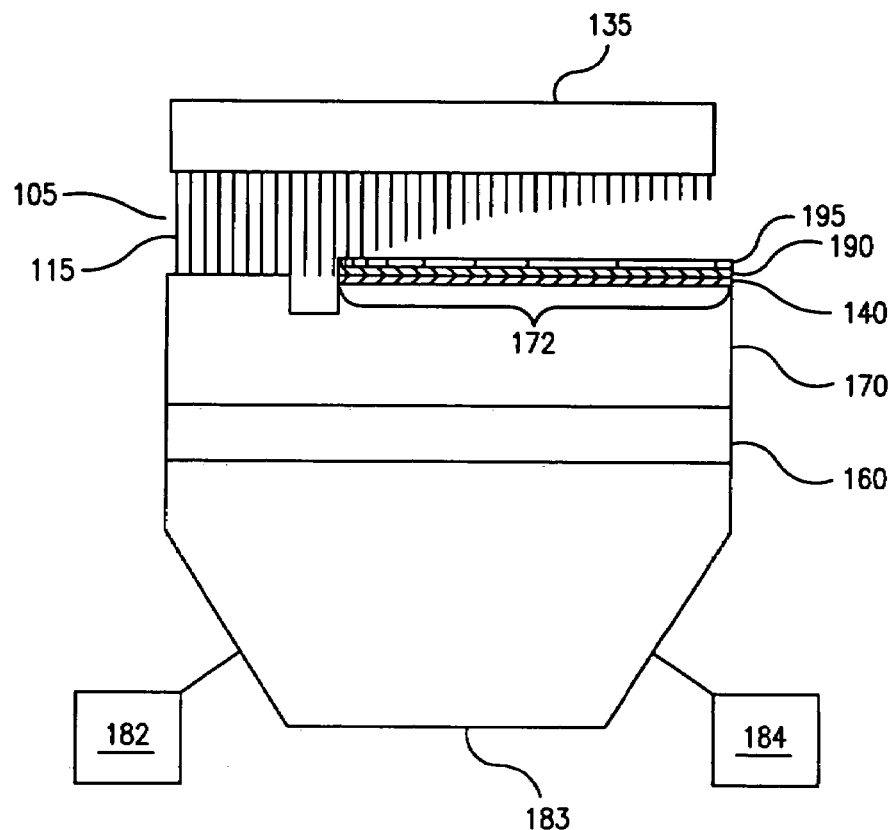

FIG. 1D illustrates the introduction of sample fluid 115 into microfluidic channel 150 through inlet 105. As analyte from sample fluid 115 passes over bound reagent 190, analyte binds to the bound reagent to form a layer of bound analyte 195. The lines of sample fluid 115 indicate the concentration of analyte molecules as analyte molecules are depleted from the sample solution as they bind to the binding wall. Consequently, a concentration gradient of bound analyte is also formed on binding wall 130.

Detection of bound analyte can be made along detection area 172 at discrete points, or along some or all of the detection area simultaneously. FIG. 1D also illustrates one schematic for surface plasmon resonance (SPR) detection of bound analyte, in which light source 182 is coupled through prism 183 to gold layer 140. Light reflected from gold layer 140 is detected at detector 184. This figure illustrates only one possibility for detection of analyte binding. Numerous other detection methods are known in the art.

Immediately downstream of the storage area it is possible, as long as there are enough capture molecules in the plug, to saturate the binding surface with that molecule. Such a region of capture molecule saturation can easily be made by another, albeit more complex, method, such as spotting. However, note that as the capture molecule plume moves downstream, the concentration on the surface drops as the concentration of capture molecules in the plume is depleted. This allows the immobilization method of this invention to produce not only a region in which the capture molecule is saturated on the surface, but a zone further from the cavity that gradually, and in a predictable and controlled manner, varies from saturation to zero. Such a concentration gradient is very useful in designing and utilizing solid phase affinity binding assays, which often require much experimentation to determine, for example, the optimal surface concentration of capture reagent. The formation of a gradient of capture molecules ensures that the optimal concentration exists at some point along the binding wall, thereby negating the need for the large amounts of experimentation necessary with traditional solid phase affinity binding assays, which allow for only one concentration per binding surface.

Figure 2:
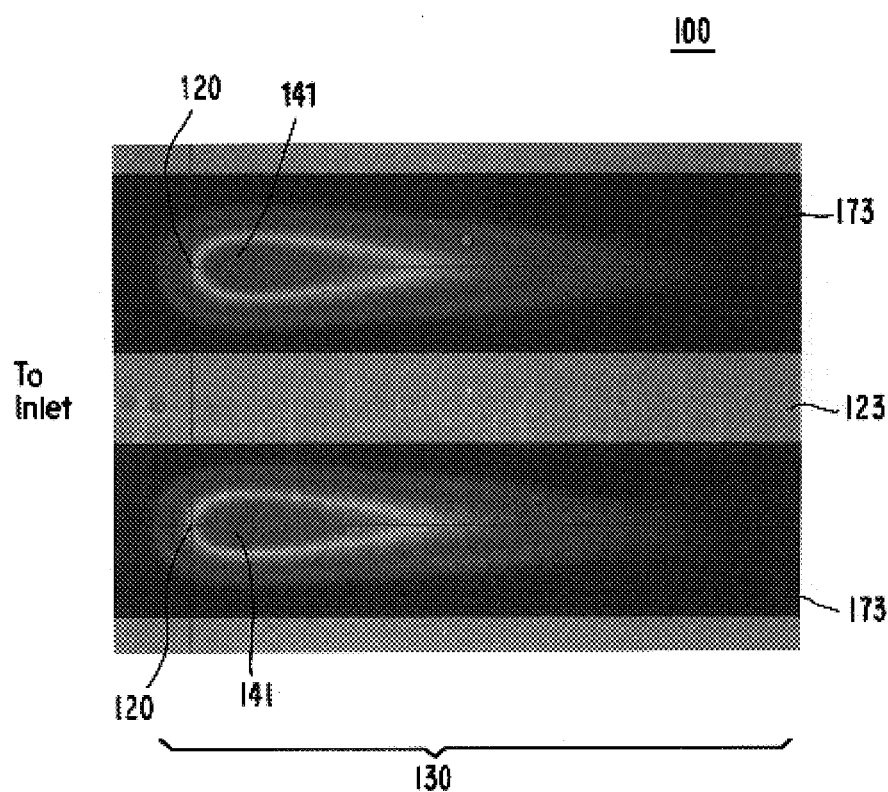
FIG. 2 illustrates one possible surface distribution of binding molecules introduced to a flowing stream from storage areas.

FIG. 2 illustrates one possible surface distribution of binding molecules introduced to a flowing stream in microfluidic device 100 from storage areas 120. Storage areas 120 are modeled here as point sources on the surface. Flow is from left to right and differences in binding densities of reagent molecules is indicated by the different shades of grey. (Note that this figure was originally presented in color, with different intensities represented by the color spectrum from red (highest concentration) to blue (lowest concentration). Conversion to grey scale resulted in loss of color information). In FIG. 2, the area of highest density for each storage area 120 is the dark area 141 to the right of storage area 120. Density decreases in the areas surrounding 141, forming a continuous, or almost continuous, surface concentration gradient of reagent molecules to the area of lowest concentration 173. A concentration gradient is present in the flowing fluid for reagent molecules that do not bind to the binding wall 130. FIG. 2 illustrates that it is possible to place storage areas sufficiently far apart to prevent the overlap of their respective reagent plumes, and thus create spaces 123 in which the binding wall remains free of bound reagent. These spaces are useful for detecting reference signals, or placement of electrodes.

Figure 3:
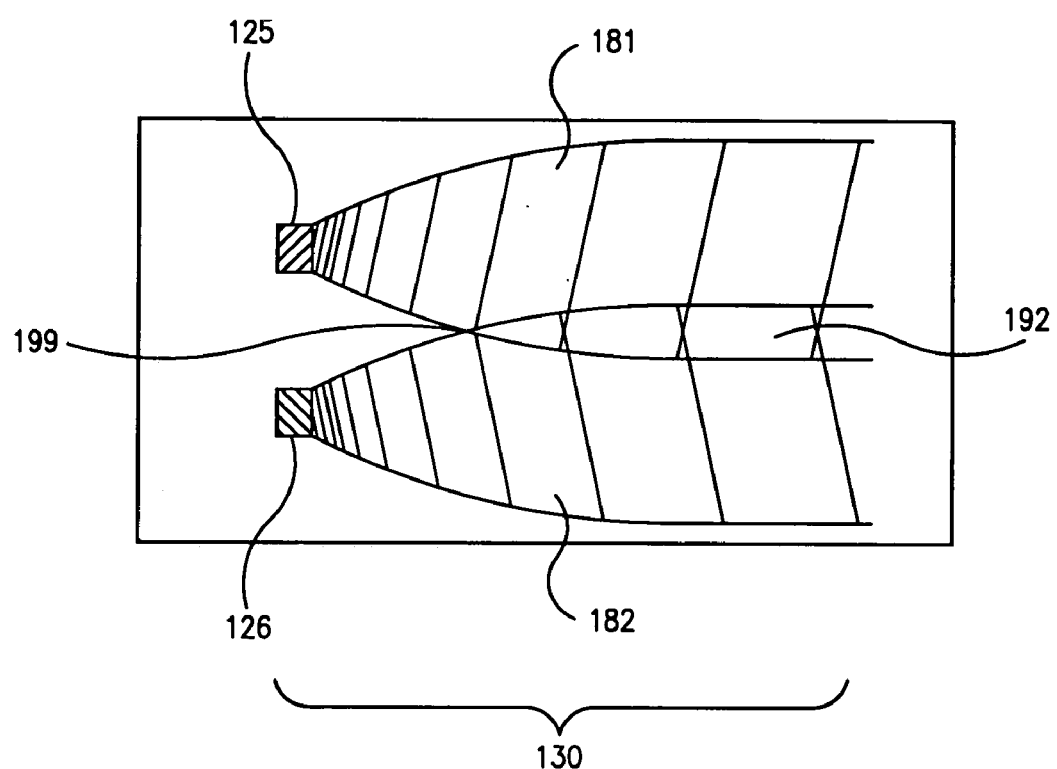
FIG. 3 illustrates one embodiment of the device of this invention wherein storage areas are placed sufficiently close together that their reagent plumes (and thus binding areas) overlap.

Alternatively, storage areas can be placed close enough to each other such that their reagent plumes overlap, allowing creation of complex, mixed surface concentration gradients. Such mixed surface concentration gradients are useful for, for example, capturing large or complex analytes that have two or more different antigens in close proximity. This could improve the affinity and selectivity of the capture molecule layer. One example of the overlap of reagent plumes is illustrated in FIG. 3, which is a top view of the bottom wall of a microfluidic device of this invention. In FIG. 3, storage areas 125 and 126 are positioned in parallel such that their reagent plumes (181 and 182, respectively) overlap at intersection point 199 along binding wall 130 to form an area of bound reagent overlap 192. This figure illustrates only one configuration of the storage areas to create reagent overlap. One of ordinary skill in the art would recognize that numerous other arrangements are possible to change the extent of overlap. For example, positioning storage areas 125 and 126 closer together would ensure greater overlap at the higher concentration gradients.

Figure 4A:
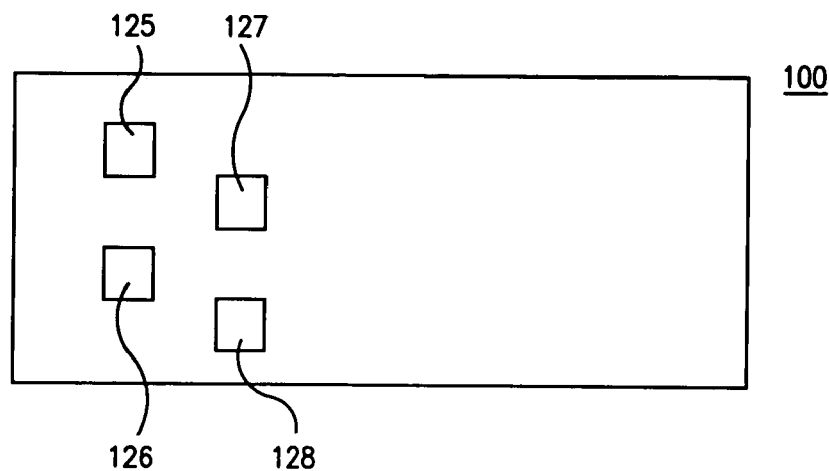
FIGS. 4A-4C show 3 possible configurations of storage areas in a 2-dimensional array.
Figure 4B:
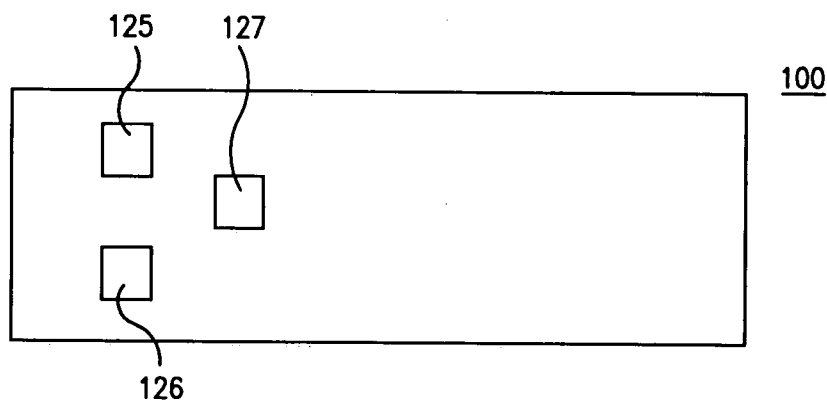
Figure 4C:
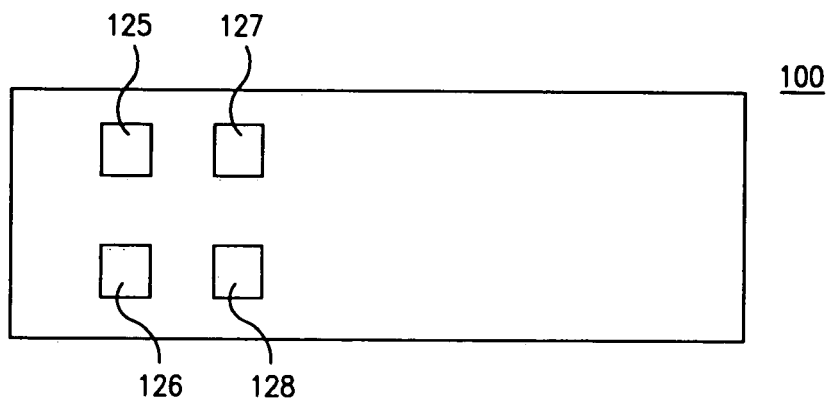

The storage areas can be placed in more complex arrays, as pictured in FIGS. 4A-4C, which show multiple storage areas 125-128 on microfluidic device 100. As described above, these storage areas can be placed such that the plumes formed upon dissolution of the reagent plugs overlap, or remain isolated.

Further variation in the formation of gradients, overlapping gradients, and the relative dissolution rates of solid reagent plugs can be achieved by varying the flow rate of the fluid during the period of dissolution of the plugs.

Once capture reagent has been immobilized to the binding surface, sample fluid containing, or suspected of containing, analyte is flowed into the microfluidic channel across the binding surface. Analyte molecules bind to the immobilized capture molecules and are either detected directly or are additionally coupled to secondary binding molecules that optionally comprise reporter molecules. In traditional solid phase affinity binding assays, including assays run in flow cells, the binding of analyte to the immobilized capture reagent is limited by diffusion of the analyte to the solid phase. The binding surface binds the analytes, and in doing so, depletes analyte concentration in the zone near the surface. Analytes close to the wall opposite the binding wall may never reach the binding wall. This invention provides a way to accelerate the capture of analytes by the binding wall (e.g. the SPR surface) beyond that which is generally achieved by simply flowing fluid across the capture surface, and thus overcome the diffusion limitations of traditional affinity binding assays.

Electrokinetic Methods for Enhancing Sample Capture Efficiency and Rate in Solid Phase Affinity Binding Assays If we assume that the principal task of the fluidics of the sensor system is to take a finite volume of sample and force as much of the analyte present to bind (selectively) to the binding wall in the minimum time, there are several problems. Let us assume that we are working in conditions in which there are very few analyte molecules available. To maximize the signal generated by bound analyte, the binding wall should be small (to maximize the number of analyte molecules per unit area). The fluid must flow over this surface to allow binding, but the thicker the microfluidic channel is in the direction perpendicular to flow (greater value of d in FIG. 1), the longer the sample fluid must be in residence in the microfluidic channel to allow analyte molecules to diffuse to the surface from the far wall. One solution to maximizing analyte binding is to minimize d and increase the flow rate of the sample fluid to compensate for the reduced total flow of sample across the detector area per unit time, but this reduces the time that the fluid spends near the binding wall and may lead to shear-induced effects on the binding strength, which can adversely affect analyte-capture reagent binding. Another solution is to put the whole sample and the binding wall in a single rapidly-stirred tank and wait for the stirring to bring all the analyte molecules into within diffusion distance from the surface. This is not necessarily the most rapid way to get all the analyte bound to the surface, because the analyte in the sample is continually diluted with time.

Electrokinetic effects such as microfluidic zone electrophoresis ($\mu$ZE) or isoelectric focusing ($\mu$IEF) transverse to flow are used herein with the microfluidic device of this invention to greatly speed the binding of analytes to the binding wall in the detection area, allowing faster flow-through rates and/or the use of thicker channels to concentrate the analyte molecules of interest close to the intended binding surface. For proteins the diffusion to the binding surface can be the limiting step in the rate of capture by that surface. Even if the target molecules are not pushed all the way onto the binding surface itself, great enhancement in the binding rate can be seen because the time for diffusion to the binding surface is so dependent on distance. Computer modeling can be useful in predicting the interaction between flow protein charge, pH, and applied voltage in these systems.

Figure 5:
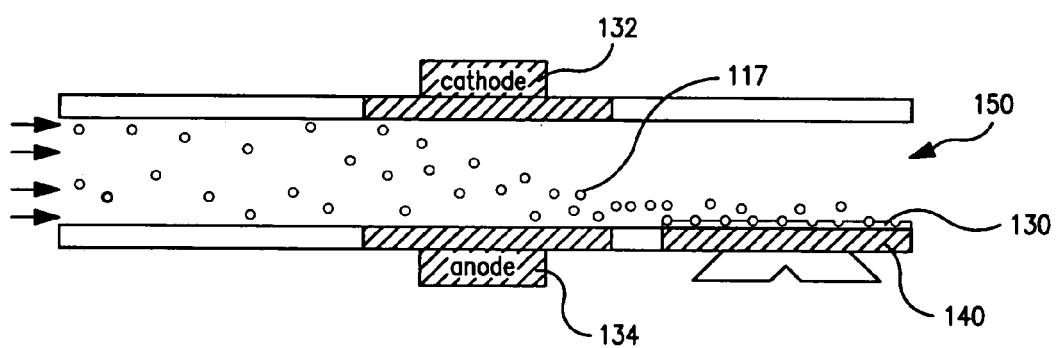
FIG. 5 illustrates one embodiment of the microfluidic device of this invention incorporating electrodes to effect the electrokinetic control of analyte.

One example of the use of electrokinetic effects to accelerate the capture of analyte flowing in the microfluidic device of this invention is shown in FIG. 5. Analyte particles 117 flowing in microfluidic channel 150 pass between electrodes 132 (cathode) and 134 (anode) upstream of binding wall 130. In this embodiment, application of a potential between anode 134 and cathode 132 results in the acceleration of analyte toward the anode, thus concentrating the analyte near binding wall 130. Many variations on the use of electrokinetics can be used to concentrate analyte at the binding wall, depending on the analyte of interest, and the analyte buffer concentrations. Such variations are well known in the art. If, for example, the buffer concentration is strong, $\mu$ZE moves particles according to their electrophoretic mobility all the way to one wall. If the buffering is light, $\mu$IEF brings analytes to focus in a plane close to the binding surface. Also, electrodes in FIG. 5 are shown as separate from the binding wall. However, if SPR is the detection method used, a gold surface 140 can be used as one of the electrodes (with the second electrode placed on the opposite wall), or the electrodes can be interdigitated with the SPR gold surface. In this case the electrodes serve to concentrate appropriately charged analytes near the capture surface, thereby increasing the method's sensitivity and/or increasing its speed. If the use of the SPR electrode as the electrode leads to excessive local changes in pH, thereby altering the binding of the analyte to the capture surface, it is possible to move the electrodes upstream of the SPR capture surface, thereby decoupling the concentration and capture steps.

Patterning Capture Molecules to Enhance Analyte Measurement

In conventional affinity binding assays, saturation of the capture molecule must never occur, because once the concentration of free analyte exceeds that required for saturation, no information on the analyte concentration in solution is available. The only way to solve this problem with an equilibrium immunoassay is to use (i.e. spend great sums to obtain or raise) capture molecules with lower affinities for the analyte in question. However, when the rate of increase of the number of analyte molecules in the surface capture layer is known, it is possible to determine the concentration of the analyte with only one type of capture molecule, even if the capture layer would eventually saturate. To get this information it is necessary to have more than one density of capture molecule on the surface. This is accomplished with the formation of surface concentration gradients of capture molecules, as provided by this invention.

Figure 6:
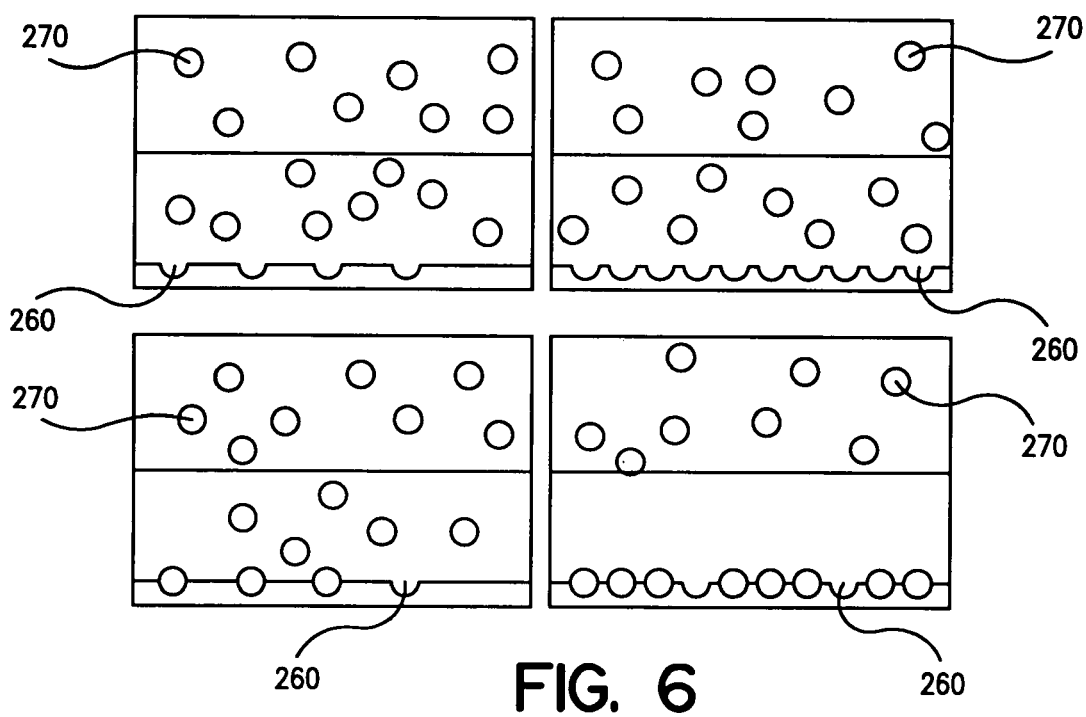
FIG. 6 is a schematic representation of the impact of density of surface capture molecules on the kinetics of reaching steady state.

FIG. 6 is a schematic representation of the impact of density of surface capture molecules on the kinetics of reaching steady state. On the top left, at low capture molecule 260 density, the final degree of site saturation by analyte molecules 270 is reached early (bottom left) because the thin layer of fluid next to the surface can supply all the analyte molecules needed to reach steady state occupancy. At the top right, if the number of capture sites is high relative to the number of analyte molecules in the near-surface fluid volume, the analyte molecules may all be captured before saturation is reached (bottom right), so the approach to saturation is dominated by diffusional transport from volumes further from the surface. (Note that the apparent discrete concentration gradient is not entirely realistic—the concentration varies continuously from one edge to the capture surface.)

Half-saturation of capture molecule binding sites (in the presence of an infinite sink of analyte) is determined only by the affinity of the analyte for the capture molecule. This is a molecular property (affected only by such things as salt concentration, temperature, etc.). In conventional solid phase affinity binding assays, as many capture molecules as possible are bound to the optically-probed zone to maximize the optical signal obtained at saturation of the sites. The present invention allows the extraction of useful information from the presence of multiple zones on the binding wall that contain identical capture molecules, but at different densities. While using lower-than-saturation densities reduces the optical signal strength, the concentration information obtained from rates of arrival of analytes to the surface of the device is of great value because it allows the measurement to be made long before steady state is achieved. The assay can be accomplished in much less time that "conventional" solid phase affinity binding assays in flow cells.

SPR Detection of Analyte Binding

One detection technique that is particularly useful in solid phase affinity binding assays utilizing the microfluidic device of this invention is SPR. When using SPR, the detection area of the microfluidic device is coated with a thin metal, preferably gold. Many different configurations of SPR are known in the art, and can be adapted for use with the present invention (e.g. Jung, L. S., et al. *Sensors and Actuators,* 1999, 54, 137-144; Lyon, L. A., et al. *Sensors and Actuators B,* 1999, 54, 118-124; Naimushin, A. N., et al., "Detection of *Staphylococcus Aureus* Enterotoxin B in Femtomolar Amounts by a Miniature Integrated Two-channel SPR Sensor", *Biosensors & Bioelectronics,* 2002, (in press); Place, J. F., et al., *Biosensors,* 1985, 1, 321-353; U.S. Pat. Nos. 5,815,278; 5,822,073; 5,991,048; 5,858,799; and U.S. patent application Ser. No. 09/566,772 filed May 8, 2000; No. 60/132,893 filed May 6, 1999; No. 60/132,895 filed May 6, 1999; and No. 60/132,894 filed May 6, 1999, all of which are incorporated herein in their entirety to the extent not inconsistent herewith).

The technique of surface plasmon resonance microscopy additionally allows interrogation of small areas of the binding surface, allowing interrogation of areas having different concentration gradients. SPR microscopy uses an expanded, collimated beam to investigate spatially resolved areas on the surface. Introduced by Rothenhausler and Knoll (Rothenhausler, B. and Knoll, W.; *Letters to Nature* 332, 615-617 (1988)), it has been extensively described (C. E. H. Berger, C.E.H., et al., *Review of Scientific Instruments* 65, 2829-2837 (1994); H. E. de Bruijn, et al., *Applied Optics* 31, 440-442 (1992); H. E. de Bruijn, et al., *Applied Optics* 32, 2426-2430 (1993); Hickel, W. and Knoll, W., *Thin Solid Films* 187, 349-356 (1990); Hickel, W. and Knoll, W., *Thin Solid Films* 199, 367-373 (1991)) and used in the scientific investigation of biological molecules (Brockman, J.M. et al., *Annual Reviews of Physical Chemisty* 51,41-63 (2000). One preferred SPR microscope for use with the microfluidic device of this invention is described in U.S. Patent Application No. 60/421,917 (incorporated herein in its entirety, to the extent not inconsistent herewith).

Point-of-care Detection System

The design of the microfluidic device of this invention lends itself to point-of-care diagnostics use or field-portability because it is extremely simple. In one embodiment of a microfluidic detection system, a single syringe pump (or other pumping system) is used to control all fluid movements.

Figure 7:
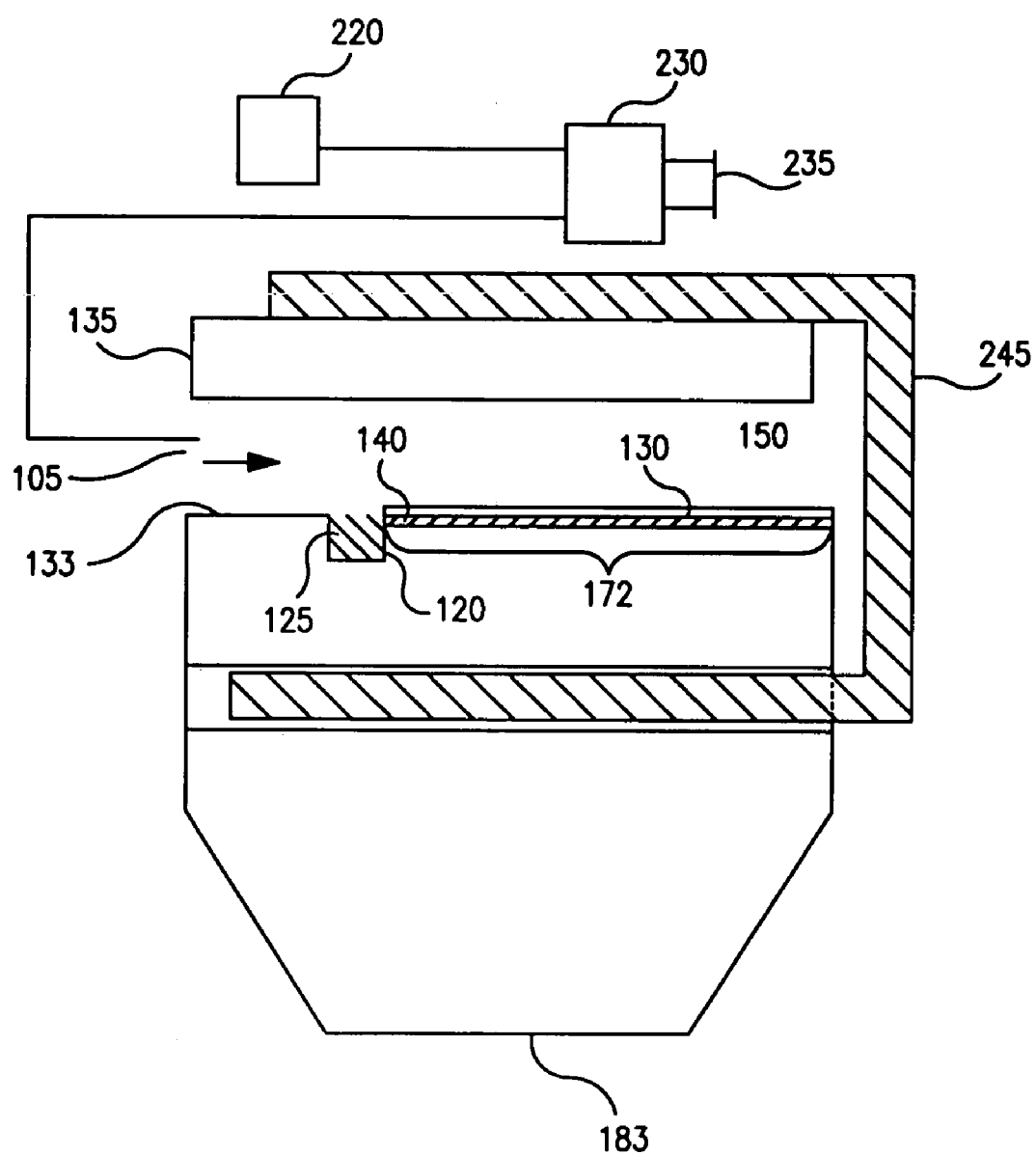
FIG. 7 illustrates one embodiment of a detection system utilizing the microfluidic device of this invention.

As shown in FIG. 7, the system comprises the microfluidic device of this invention, the inlet 105 is in fluidic connection with single displacement pump 230 which initially contains a wetting fluid and which is also in fluidic connection with sample reservoir 220. To operate the system, in this simple form, handle 235 of pump 230 is depressed to push the wetting fluid into microfluidic channel 150, where it dissolves the reagent plug 125 and carries the dissolved or suspended reagent to binding wall 130. When handle 235 is pulled back out, sample fluid is drawn into the body of pump 230 from sample reservoir 220. Pushing handle 235 a second time introduces sample fluid into microfluidic channel 150 where it flows across, and binds to reagent bound on binding wall 130. The system further comprises an optical detection system such as an SPR system, including prism 183, which utilizes a thin metal film 140 as the binding wall. During the second injection into the microfluidic channel, a CCD camera records SPR images and uses them to calculate the concentration of analytes in the sample. Inexpensive, disposable prisms may be used and permanently fixed to the microfluidic device, or a device holder 245 may be used to align the microfluidic device with the SPR optics. The instrument can be used downstream of a sample collector such as an air sampler for Chemical and Biological Warfare (CBW) agent detection, or can directly aspirate fluid samples like blood.

The microfluidic devices of this invention can be formed by any method known in the art, including the etching of solid substrates such as glass or silicon, or by the formation of polymeric laminate structures from materials such as Mylar and poly(dimethylsiloxane) (PDMS).

Devices in which spots on one or more of the microfluidic channel walls form the storage areas typically comprise the following layers (from the bottom up): a glass slide, 6 mil ACA (adhesive, carrier, adhesive) with a 2 mm wide uniform channel having an inlet and outlet, and a 10 mil Mylar top sheet.

Figure 11:
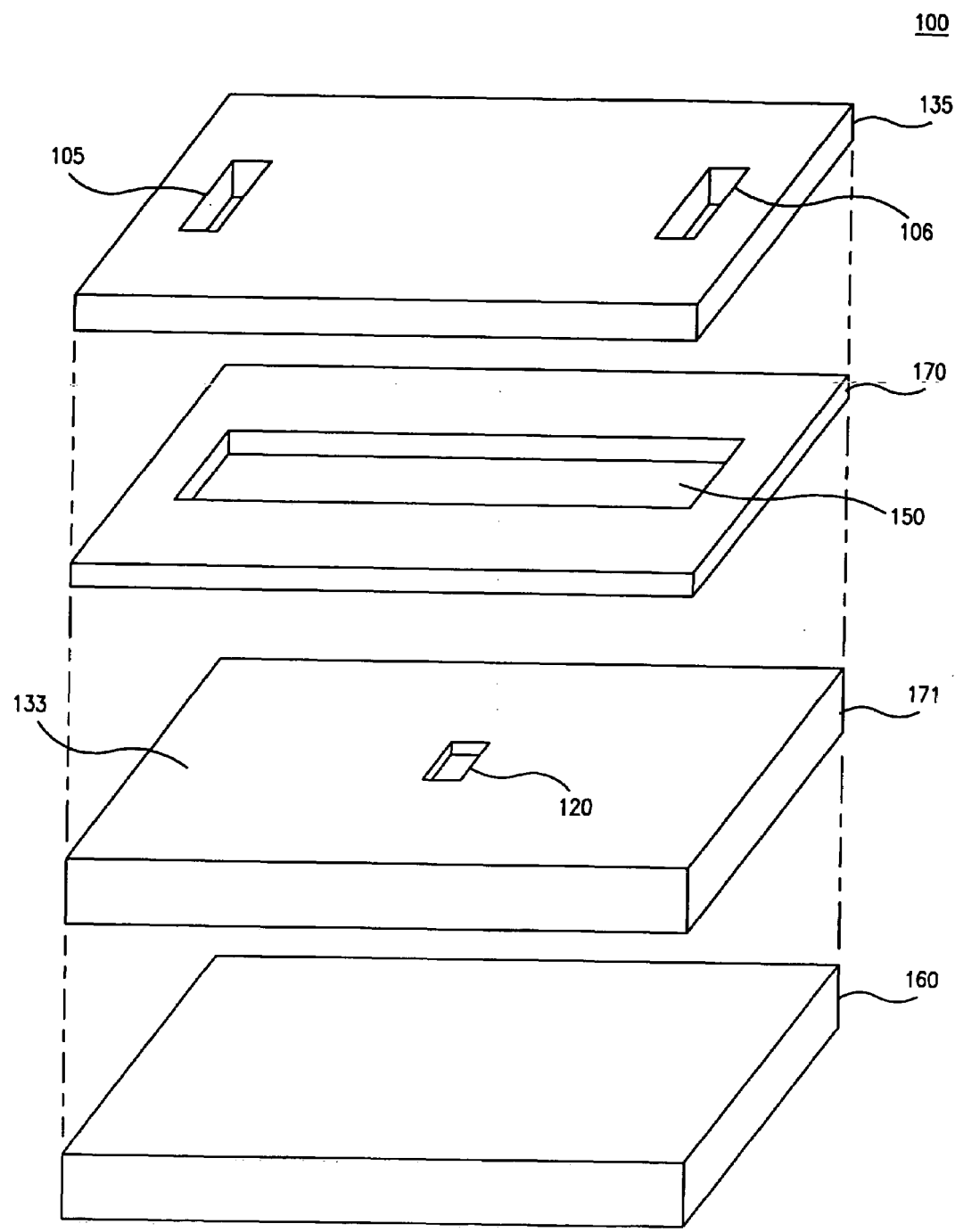
FIG. 11 is an exploded view of a laminate structure used to form one embodiment of the microfluidic device of this invention.

Devices comprising cavities as storage areas typically comprise more layers in their laminate structure. One general structure (not to scale) illustrating one possible laminate structure (blown apart) is shown in FIG. 11. The laminate structure in FIG. 11 comprises four layers. Base 160 is used for overall structural support of the device. Layer 171 is adhered to base 160 and also comprises cavity 120 and serves as the bottom wall for microfluidic channel 150, which is formed by cutting through substrate 170. Coverplate 135 is layered on substrate 170 to form the top wall of the microfluidic channel, and also optionally comprises inlet 105 and outlet 106.

Two examples of such laminate structures include the following Mylar and PDMS structures:

Mylar structures typically comprise the following layers (from bottom to top): glass slide; 6 mil ACA with a circular hole (this forms the cavities; this hole ranges from 200 μm to 1.5 mm); 10 mil Mylar with same size circular hole; 6 mil ACA with a 2 mm wide channel with inlet and outlet placed such that the cavity is approximately ⅙ down the length of the channel on the inlet side; 10 mil Mylar top sheet.

PDMS structures typically comprise the following layers (from top to bottom): glass slide, PDMS with cavity 200 μm wide and 200 μm deep, 10 mil ACA with a 2 mm wide channel with inlet and outlet placed such that the cavity is approximately ⅙ the way down the length of the channel on the inlet side, 10 mil Mylar top sheet.

The specific thicknesses, materials, numbers of and configurations of the laminate layers recited in these descriptions of these typical devices and the drawings are exemplary only. Those of ordinary skill in the art would recognize that other materials and thicknesses could be used on condition that they satisfy particular optical or chemical requirements for a given device or application. Also, the microfluidic device of this invention can be used in conjunction with other microfluidic elements known in the art such as sample pre-filters, sample storage channels, flow cytometers, electrophoretic separators, and the like.

EXAMPLES

I. Evaluation of Formation and Dissolution of Solid Reagent Plugs

A model system utilizing fluorescein as the reagent in buffer with varying weights of the preservative trehalose and/or dextran, was used to evaluate the formation and dissolution of solid reagent plugs in a microfluidic device of this invention. The following solution sets were utilized for these experiments:

A. Solution Set I—fluorescein+trehalose in buffer

Stock buffer/fluorescein solution: 100 mM Tris $HNO_3$ buffer with 2 mM KCl and 0.10 mM $MgCl_2$ and 20 µM fluorescein at a pH 7.8. The stock buffer/fluorescein solution was combined with varying percentages of crystalline trehalose dihydrate obtained from Sigma Chemicals Inc., in order to determine whether the percentage of trehalose would affect how well the drying proceeded. It proved desirable to use a solution with the highest weight % of trehalose possible because this is closest to the end-state of drying desired (the lowest water percentage possible). The solubility of trehalose in pure water is approximately 40%. The solutions created contained mass percentages of trehalose from 2% to 40%.

B. Solution Set II—Solutions from Set I+Dextran

Acting on the hypothesis that dextran would increase the dissolution time of the dried product, solutions containing various weight percentages of the stock buffer/fluorescein solution (from above), trehalose, and dextran (obtained from Sigma Chemicals, Inc.; avg. molecular weight 68,000 Da) were created. The percentage of trehalose ranged from 10% to 35% and the percentage of dextran ranged from 1% to 25%.

C. Solution Set III

To quantitatively graph the fluorescein concentrations downstream, solutions containing a higher concentration of fluorescein were created. The concentration of the stock buffer/fluorescein solution was increased from 20 µM to 400 µM. It had been determined that the greater the % dextran, the longer the dissolution time, so solutions containing 5% to 25% dextran and 15% to 40% trehalose were created from the stock buffer/fluorescein solution.

Solution Set IV:

An even greater fluorescein concentration was needed in order to detect the concentration of fluorescein downstream, so the concentration of fluorescein in the trehalose/buffer stock solution was increased to 6 mM. The same combination of weight percentages of dextran and trehalose as made in the third set of solutions was used for these solutions.

Drying

The solutions described above were deposited on the microfluidic devices of this invention as either spots, or in cavities. Cavities and spots were loaded by using a pipetman and a stretched glass capillary tube to obtain a hollow dispensing "needle" approximately 200 µm wide. The microfluidic devices were then placed in the laminar flow hood and dried for varying amounts of time.

Variables modified: solution composition, whether drops of solution were placed in cavities or on glass slides, cavity composition (Mylar, Teflon tubing or PDMS), drying time. After being placed in a laminar flow hood for 48 hours, the solutions containing both trehalose and dextran dried to a uniform consistency much like glass. This glassy product is obtained either for drops on glass or drops in cavities. The higher the percentage of dextran, the more glass-like the product. Additionally, the dried product was more uniform when the solutions were dried in narrow-bore Teflon tubing and PDMS cavities, as opposed to cavities in Mylar.

Dissolution Experiments

Dissolution target parameters:

(1) The dried material must dissolve between 2 and 10 minutes at a flow rate in the channel of approximately 1 mm/sec.

(2) The dissolution should produce a plume of reagent (fluorescein) downstream that is reproducible and predictable, preferably modelable).

(3) The dried material must be contained within a space small enough that multiple dried dots can be placed side-by-side within a typical width microfluidic channel. Evaluation of the dissolution experiments:

Drops on Glass Slides

Variables modified: solution composition (among first and second set of solutions), drying process used, size of drop (up to 0.5 µl), flow rate in the channel (0.1-1 mm/sec)

Experimental results: Drops on the surface (about 1.5 mm wide) dissolved completely in about 20-90 seconds. Higher dextran concentrations and air drying yielded longer dissolution times. Dissolution was most reproducible when air-drying was used (which produces a relatively uniform dried material without excessive irregularities.

Drops in Cavities

Variables modified: solution composition, drying process used, size of cavity, composition of cavity, extent of filling cavity, flow rate in the channel.

Experimental Results:

Mylar cavities: Cavities that were 200 µm wide and 400 µm deep could be used to produce reasonably acceptable results. Dissolution times ranged from 3-10 minutes, with higher times corresponding to higher dextran concentrations.

PDMS cavities: PDMS cavities produced much more reproducible dissolution results, perhaps because the PDMS cavities were smoother. Dissolution times ranged from 4-10 minutes. The range of times was probably due to inconsistent filling protocols.

The solution that produced the most uniform solid reagent plugs having dissolution results within the target parameters, and the method used to make it, comprised: Solution. ~30% by weight trehalose dihydrate, approx. 20% by weight of dextran (obtained from Sigma chemicals, Inc.; avg. molecular weight 68,000), and approx. 50% by weight of a stock buffer/fluorescein solution (100mM Tris $HNO_3$ buffer with 2mM KCl and .10mM $mgCl_2$ and 20 µM fluorescein at a pH 7.8).

Solution Preparation: Approximately 1 ml of the above solution was prepared in 1.5 ml microcentrifuge tubes. 500 µl of the stock buffer/fluorescein solution was pipetted into the centrifuge tubes. To this, 0.3 g of trehalose and 0.2 g of dextran were added. Slight heat and agitation was necessary for complete dissolution of the dextran.

Figure 8:
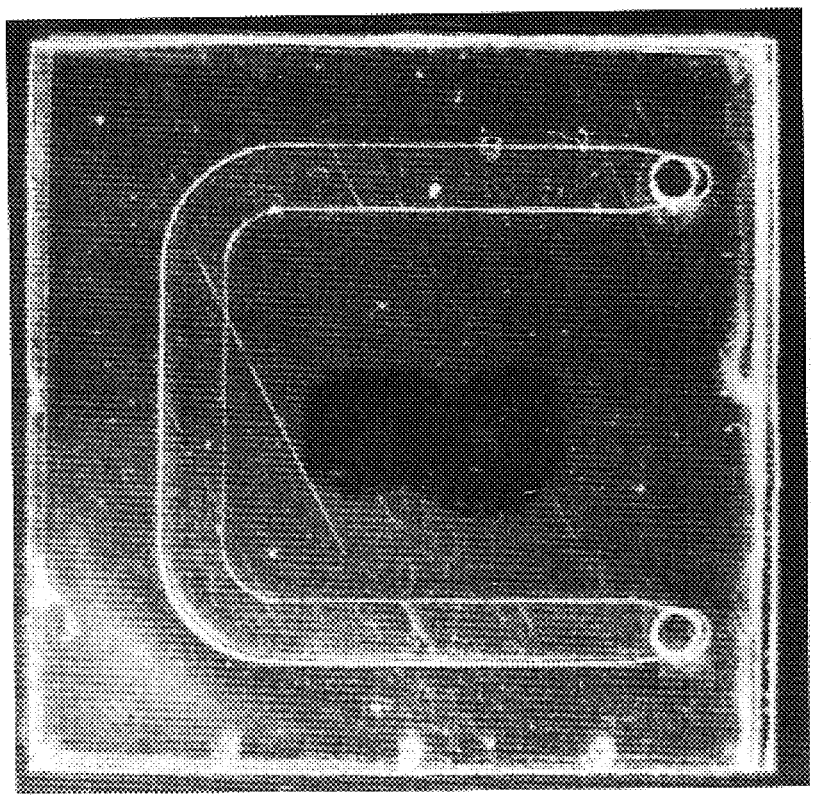
FIG. 8 is a photomicrograph one embodiment of a poly (dimethylsiloxane) (PDMS) microfluidic device.

The PDMS device pictured in FIG. 8 was used to measure dissolution. The PDMS device is described above, and was formed by the following steps:

1. Pretreatment of the substrate: A photoresist mold was placed on a silicon substrate wafer four inches in diameter. This substrate was not treated with acid prior to use.
2. Coating the silicon wafer substrate: Approximately 5 ml of NANO SU-8 photoresist was placed on the silicon wafer and spun for approximately 20 seconds at 750 rpm.
3. Soft Bake: After the wafer was coated evenly with the photoresist, it was baked on a level hot plate. Step 1: baked at 65 degrees Celsius for 30 minutes. Step 2: baked at 95 degrees Celsius for 90 minutes. Step 3: allowed to cool on a level area for 15 minutes.
4. Exposure: Subsequently, the wafer with photoresist was exposed to near UV (350-400 nm) radiation for a total time of 16 minutes with a break of 1 minute every 4 minutes. A transparency mask was used to selectively choose which portions of the photoresist would become cross-linked (only the exposed portions) and therefore which portions would permanently be raised from the surface of the substrate.
5. Postbake: on level hot plate. Step 1: 65° C. for 15 minutes. Step 2: 95° C. for 25 minutes.
6. Develop: using MicroChem SU-8 developer. The wafer was placed in a container with enough developer to cover it, and agitated for 5 minutes. Next, the old solution was replaced with new solution and the wafer was agitated for another 10 minutes.
7. Rinse and Dry: Finally, the wafer was rinsed with isopropyl alcohol and then dried with nitrogen. Inspection under a microscope confirmed that the raised portions (which form the PDMS "holes") were approximately 200 μm deep.
8. Creating the PDMS mold: Sylgard brand silicon elastomer was mixed with curing agent in the ratio of 10:1 (by weight) and degassed in a standard bell-jar dessicator. The completed photoresist mold was placed in the bottom of a Petri dish and the PDMS was poured over the mold so that its surface raised only 1 ml above the high portions of the photoresist mold. The Petri dish was then placed in a dessicator for further degassing, then placed in an oven at 65° C. for 2 hours to cure the PDMS.
9. Creating the Laser-cut channel: The design for the channel was created on AutoCad. The Universal Laser System $CO_2$ cutting tool in the Washington Technology Center was used to cut the outline of this channel in 6 mil ACA from Fralock, Inc.

After formation of the PDMS squares (25 mm on a side, the same size as a glass slide) with the cavities, each layer of the PDMS device except the top Mylar sheet was assembled. The cavities were loaded with the preferred trehalose/dextran/buffer solution using a stretched capillary tube on the end of a pipetman, and allowed to dry in a laminar flow hood for 48 hours. After the drying was complete, the Mylar top sheet was placed on the device.

Testing the Dissolution of the Dried Solution:

The dissolution was tested using a Kloehn stepper-motor driven pump system and a custom-built manifold to hold the device. Deionized water was passed through the channel and over the cavity at a velocity of approximately 0.5 mm/sec. Images were captured on VHS tape using a COHU color video camera. Using videotape of the dissolution downstream, intensity measurements perpendicular to the flow of the stream were taken at 10 sec, 20 sec, 30 sec, 1 min, 1 min 30 sec, 2 min, 2 min 30 sec, etc, up to 9 min and 30 seconds.

Figure 9:
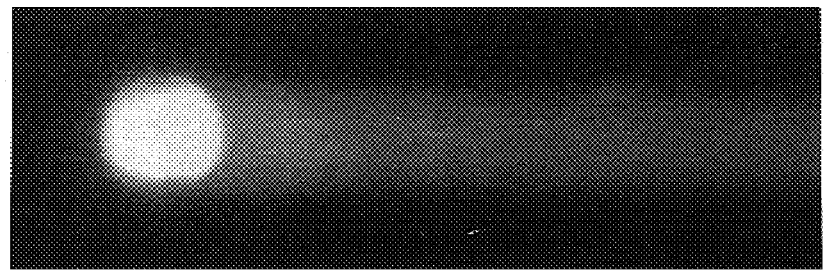
FIG. 9 is a fluorescence micrographic image of sample dissolving from a storage area.
Figure 10:
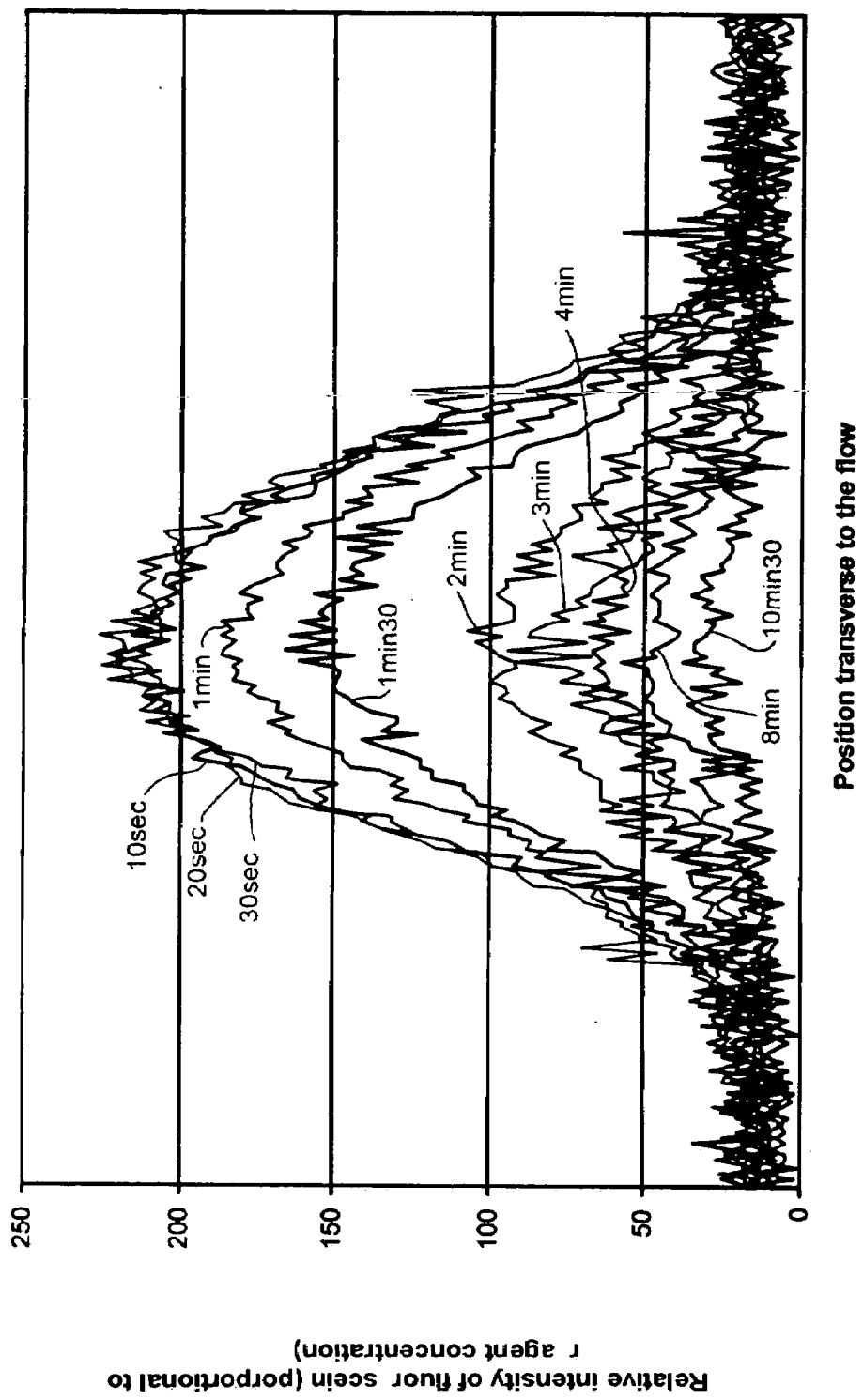
FIG. 10 is a graph of fluorescence intensity vs position in the microfluidic channel for samples dissolving from a storage cavity.

Results:

A fluorescence micrographic image of the dissolving solid reagent plug is shown in FIG. 9. A graph of the raw fluorescence intensity data with position across the flow direction (vertical slice of the image as shown in FIG. 9) and at times up to 10.5 minutes is shown in FIG. 10.

All references cited herein are incorporated in their entirety to the extent not inconsistent herewith.

Those skilled in the art will appreciate that the invention described herein is susceptible to variations and modifications other than those specifically described. It is to be understood that the invention includes all such variations and modifications which fall within its spirit and scope.

We claim:

1. A microfluidic device for detecting the presence of an analyte in a fluid sample comprising:

a) a microfluidic channel comprising a bottom wall, two side walls and a top wall and having an upstream end and a downstream end;
   b) a fluid inlet in fluidic connection with the microfluidic channel;
   c) a storage area on one of the walls of the microfluidic channel downstream of the fluid inlet;
   d) at least one dissolvable solid reagent plug fixed in the storage area, the plug comprising a matrix material and a reagent having an affinity for binding to the analyte, wherein the storage area is positioned as to allow dissolution of the reagent into a carrier fluid flowing in the microfluidic channel; and
   e) a detection area comprising a binding wall comprising a coating having an affinity for the reagent, the detection area positioned within the microfluidic channel and downstream of the carrier fluid inlet and the storage area such that the reagent dissolved in the carrier fluid binds to the coating and forms a gradient of bound reagent.

2. The microfluidic device of claim 1 wherein said detection area further comprises a linking reagent bound to said binding wall.

3. The microfluidic device of claim 1 wherein the microfluidic channel is made from a material selected from the group consisting of: metals, polymers, glasses, and combinations thereof.

4. The microfluidic device of claim 1 wherein at least one of the walls in said detection area is transparent.

5. The microfluidic device of claim 1 wherein at least a portion of said binding wall is coated with a metal.

6. The microfluidic device of claim 5 wherein the wall opposite said binding wall also comprises a metal and wherein said two metal walls are capable of being in electrical connection with each other.

7. The microfluidic device of claim 1 wherein said storage area is a cavity positioned to allow said solid reagent therein to diffuse into a carrier fluid flowing in said microfluidic channel.

8. The microfluidic device of claim 1 wherein said storage area is a spot upon which said solid reagent is fixed.

9. The microfluidic device of claim 1 further comprising a second storage area, on one of said walls of said microfluidic channel downstream from said inlet, for introducing a second reagent into the carrier fluid in the microfluidic channel.

10. The microfluidic device of claim 9 wherein said second storage area is positioned downstream from said first storage area.

11. The microfluidic device of claim 9 wherein said second storage area is positioned parallel to said first storage area.

12. The microfluidic device of claim 1 comprising a plurality of storage areas, connected to said microfluidic channel downstream from said fluid inlet, for introducing second and subsequent reagents into a carrier fluid in the microfluidic channel, said storage areas being positioned in parallel with each other.

13. The microfluidic device of claim 1 comprising a plurality of storage areas, connected to said microfluidic channel downstream from said fluid inlet, for introducing second and subsequent reagents into the carrier fluid in the microfluidic channel, said storage areas being positioned in series with each other.

14. The microfluidic device of claim 1 wherein said microfluidic device further comprises a plurality of storage areas, connected to said microfluidic channel downstream from said fluid inlet, for introducing second and subsequent reagents into a carrier fluid in the microfluidic channel, said storage areas being positioned in an array.

15. The microfluidic device of claim 1 wherein said microfluidic device further comprises:
   a) a second inlet into said microfluidic channel in fluidic connection with a tributary microfluidic channel;
   b) a second storage area disposed within said tributary microfluidic channel upstream of where said tributary channel joins said microfluidic channel; and
   c) a second dissolvable solid reagent plug fixed in said second storage area, said second reagent plug comprising a secondary reporter molecule having affinity for said analyte.

16. The microfluidic device of claim 1 wherein said solid reagent plug comprises a second reagent selected from the group consisting of: a flow-rate monitoring compound, a dissolution-rate monitoring compound, and a pH indicator.

* * * * *